(12) United States Patent
Uchiyama et al.

(10) Patent No.: US 6,903,815 B2
(45) Date of Patent: Jun. 7, 2005

(54) OPTICAL WAVEGUIDE SENSOR, DEVICE, SYSTEM AND METHOD FOR GLUCOSE MEASUREMENT

(75) Inventors: Kenichi Uchiyama, Kanagawa (JP); Ichiro Tono, Kanagawa (JP); Hideo Eto, Kanagawa (JP); Miki Nagatomo, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 218 days.

(21) Appl. No.: 10/302,685

(22) Filed: Nov. 22, 2002

(65) Prior Publication Data

US 2003/0225322 A1 Dec. 4, 2003

(30) Foreign Application Priority Data

| Nov. 22, 2001 | (JP) | ................................. P2001-358333 |
| Jan. 16, 2002 | (JP) | ................................. P2002-007807 |
| Jan. 16, 2002 | (JP) | ................................. P2002-007808 |
| May 15, 2002 | (JP) | ................................. P2002-140055 |

(51) Int. Cl.[7] ............................... G01N 33/28; G01J 3/00; G02B 6/00
(52) U.S. Cl. ..................... 356/305; 356/39; 356/300; 385/12; 385/141; 422/82.11
(58) Field of Search .................... 356/39, 300, 305, 356/317; 422/82.05, 82.09, 82.11, 82.08; 385/12, 14, 37, 129, 130, 131, 141; 250/227.11

(56) References Cited

U.S. PATENT DOCUMENTS 4,877,747 A * 10/1989 Stewart ....................... 436/525
5,071,248 A * 12/1991 Tiefenthaler et al. ....... 356/128
5,082,629 A * 1/1992 Burgess et al. ........... 422/82.11
5,094,517 A    3/1992 Franke
5,577,137 A    11/1996 Groger et al.
6,289,144 B1 * 9/2001 Neuschafer et al. .......... 385/12
6,510,263 B1 * 1/2003 Maisenholder et al. ....... 385/37
6,752,942 B2 * 6/2004 Kim et al. ................... 264/112
6,776,962 B1 * 8/2004 Boss et al. ............... 422/82.11

FOREIGN PATENT DOCUMENTS

| JP | 05-142142 | 6/1993 |
| JP | 05-332937 | 12/1993 |
| JP | 09-061346 | 3/1997 |
| JP | 11-271217 | 10/1999 |
| JP | 2000-146836 | 5/2000 |
| JP | 2001-183292 | 7/2001 |
| WO | WO 00/19203 | 4/2000 |

* cited by examiner

*Primary Examiner*—Layla Lauchman
(74) *Attorney, Agent, or Firm*—Pillsbury Winthrop LLP

(57) ABSTRACT

An optical waveguide sensor for glucose measurement comprises a substrate, a first optical waveguide layer formed on a surface of the substrate, an entrance grating and an exit grating which are formed contacting with the first optical waveguide layer and being spaced from each other, a second optical waveguide layer located between the entrance grating and the exit grating while being in contact with the first optical waveguide layer, the second optical waveguide layer having a higher refractive index that that of the first optical waveguide layer, and a functioning layer containing an enzyme and a coloring reagent which is formed on the second optical waveguide layer.

20 Claims, 17 Drawing Sheets

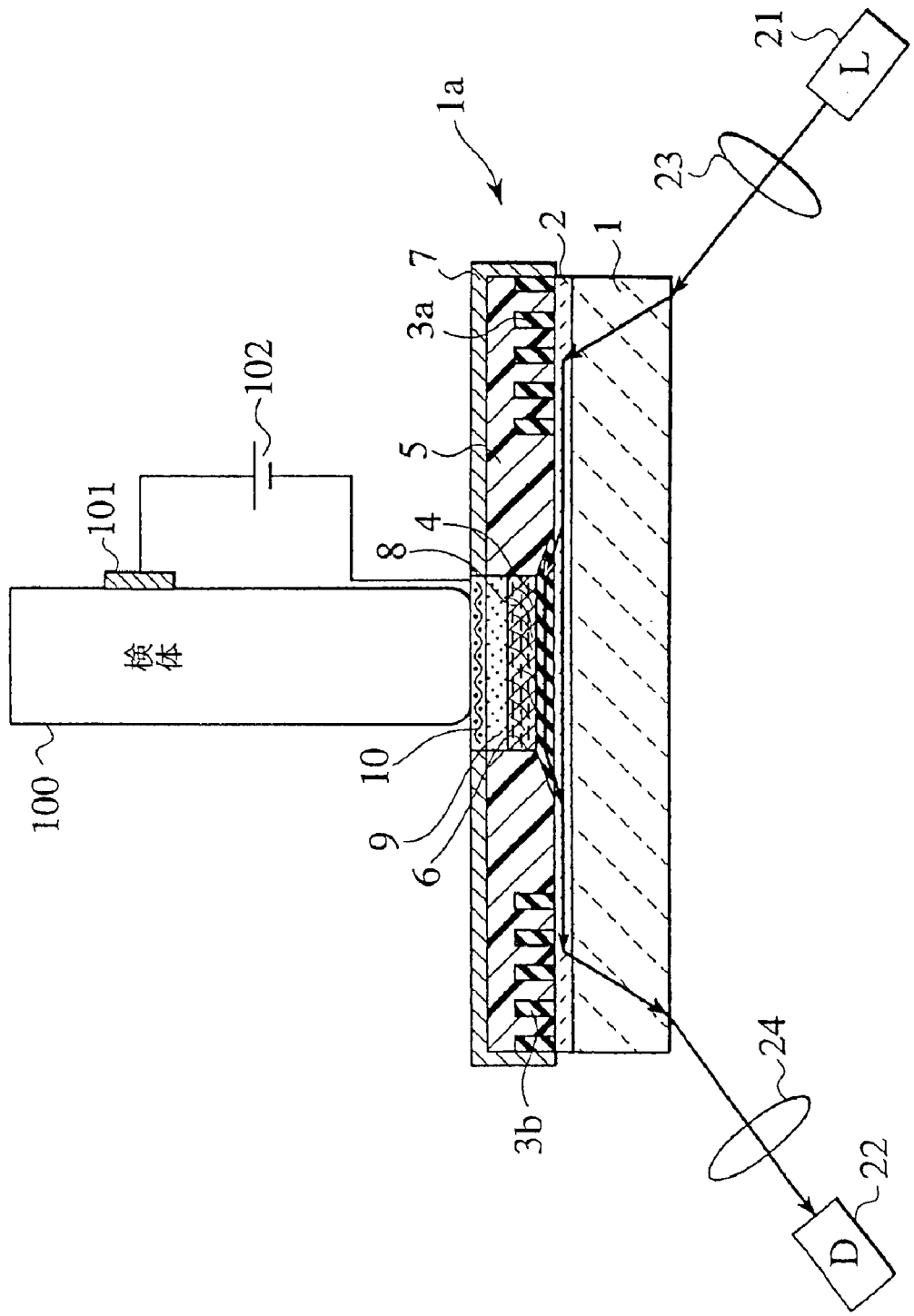

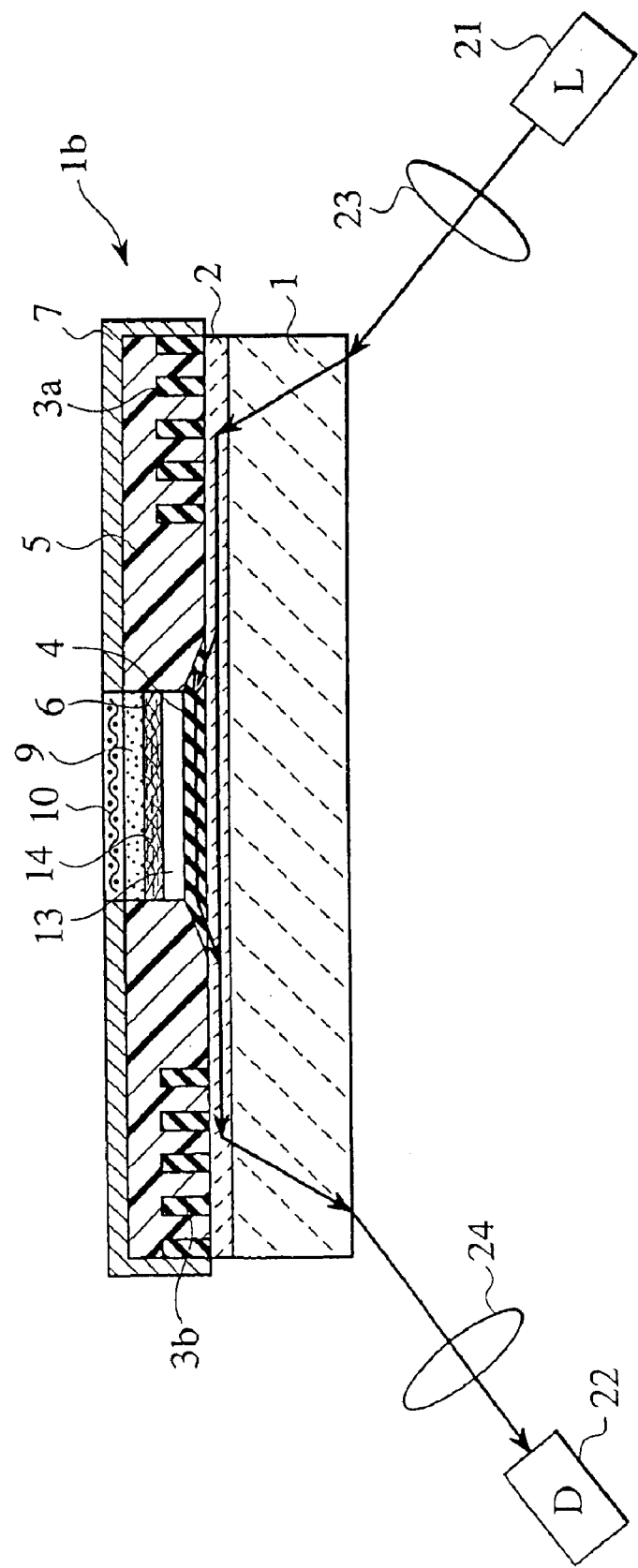

OPTICAL WAVEGUIDE SENSOR, DEVICE, SYSTEM AND METHOD FOR GLUCOSE MEASUREMENT

CROSS REFERENCE TO RELATED APPLICATIONS

This application is based upon and claims the benefit of priority from the prior Japanese Patent Applications No. P2001-358333, filed on Nov. 22, 2001, No. P2002-7807, filed on Jan. 16, 2002, No. P2002-7808, filed on Jan. 16, 2002 and No. P2002-140055, filed on May 15, 2002; the entire contents of which are incorporated herein by reference.

BACKGROUND OF THE INVENTION

1. Field of the Invention

The present invention relates to a glucose sensor, and especially relates to an optical waveguide type glucose sensor, a device for optical waveguide type glucose measurement, a system for optical waveguide type glucose measurement and a methodology for optical waveguide type glucose measurement for measuring glucose concentration in a solution such as blood.

2. Description of the Related Art

In the Japanese Patent Laid-Open Publication No. Hei 9 (1997)-61346, for example, a planar optical waveguide type glucose sensor has been disclosed. This glucose sensor has a structure in which a pair of gratings, to/from which a light comes in/goes out, are formed on a surface of a substrate, a single optical waveguide layer is formed on a part of the surface of the substrate which is located between the gratings, and a film which has molecular recognition and information transformation function is formed on the optical waveguide layer.

In the glucose sensor made up from such a structure, biomolecules contained In blood and the like are analyzed as follows. The biomolecules contained in blood extracted from an analyte are kept in contact with a film which has molecule recognition and information transformation function. A light such as a laser light is made incident to an optical waveguide layer via a grating. An evanescent wave is generated. A change in the quantity of the evanescent wave due to a reaction of the biomolecules contained in blood and the like on a film provided on the optical waveguide layer is detected by a light detector which receives the light emanating from the grating. Thus, analysis of the biomolecules contained in blood and the like is realized.

However, in the conventional glucose sensor there have been problems, such as, since the optical waveguide layer is made up with a single layer, there is a limit to the sensitivity in detecting the change in the quantity of the evanescent wave generated in the optical waveguide layer, and also the film structure on the optical waveguide layer is not suitable for analysis of the extremely small amounts of biomolecules contained in blood and the like which are extracted from the analyte.

The intention of the present invention is to provide an optical waveguide type glucose sensor which enables highly sensitive and highly accurate analysis of extremely small amounts of glucose contained in a body fluid, for example, extracted from an analyte, a device for optical waveguide type glucose measurement by use of the optical waveguide type glucose sensor, a system for the optical waveguide type glucose measurement and a methodology for the optical waveguide type glucose measurement.

SUMMARY OF THE INVENTION

According to a first aspect of the present invention, an optical waveguide sensor for glucose measurement comprises a substrate, a first optical waveguide layer formed on a surface of the substrate, an entrance grating and an exit grating which are formed contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer and a functioning layer containing an enzyme and a coloring reagent which is formed on the second optical waveguide layer.

According to a second aspect of the present invention, an optical waveguide sensor for glucose measurement comprises a substrate, a first optical waveguide layer formed on a surface of the substrate, an entrance grating and an exit grating which are formed contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer, an immobilized coloring reagent layer containing coloring reagent formed on the second optical waveguide layer and an immobilized enzyme layer containing an enzyme formed on the immobilized coloring reagent layer.

According to a third aspect of the present invention, an optical waveguide sensor for glucose measurement comprises a substrate, a first optical waveguide layer formed on a surface of the substrate, an entrance grating and an exit grating which are formed contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer, an immobilized coloring reagent layer containing a coloring reagent formed on the second optical waveguide layer and an immobilized enzyme-catalyst layer containing an enzyme and a catalyst formed on the immobilized coloring reagent layer.

According to a fourth aspect of the present invention, an optical waveguide device for glucose measurement comprises (1) an optical waveguide sensor comprising a substrate, a first optical waveguide layer formed on a surface of the substrate, an entrance grating and an exit grating contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer and a functioning layer containing an enzyme and a coloring reagent formed on the second optical waveguide layer, and (2) a detection unit comprising a light source configured to emit a light to the first optical waveguide layer, a light detector configured to receive the light coming from the first optical waveguide layer, a central process control unit configured to control a light quantity of the light source and process signals from the light detector, a memory configured to store data from the central process control unit and a display configured to display the data.

According to a fifth aspect of the present invention, an optical waveguide device for glucose measurement comprises (1) an optical waveguide sensor comprising a substrate, a first optical waveguide layer formed on a surface of the substrate, an entrance grating and an exit grating contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer, an immobilized coloring reagent layer containing a coloring reagent formed on the second optical waveguide layer and an immobilized enzyme layer containing an enzyme formed on the immobilized coloring reagent layer, and (2) a detection unit comprising a light source configured to emit a light to the first optical waveguide layer, a light detector configured to receive the light coming from the first optical waveguide layer, a central process control unit configured to control a light quantity of the light source and process signals from the light detector, a memory configured to store data from the central process control unit and a display configured to display the data.

According to a sixth aspect of the present invention, an optical waveguide device for glucose measurement comprises (1) an optical waveguide sensor comprising a substrate, a first optical waveguide layer formed on a surface of the substrate, an entrance grating and an exit grating contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer, an immobilized coloring reagent layer containing a coloring reagent formed on the second optical waveguide layer and an immobilized enzyme layer containing an enzyme formed on the immobilized coloring reagent layer, and (2) a detection unit comprising a light source configured to emit a light to the first optical waveguide layer, a light detector configured to receive the light coming from the first optical waveguide layer, a central process control unit configured to control a light quantity of the light source and process signals from the light detector, a memory configured to store data from the central process control unit and a display configured to display the data.

According to a seventh aspect of the present invention, an optical waveguide system for glucose measurement comprises (a)(1) an optical waveguide device comprising an optical waveguide sensor having a substrate, a first optical waveguide layer formed on a surface of the substrate, an entrance grating and an exit grating contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer, a functioning layer containing an enzyme and a coloring reagent formed on the second optical waveguide layer and a meshed electro-conductive thin film positioned above the functioning layer, and (2) a detection unit having a light source configured to emit a light to the first optical waveguide layer, a light detector configured to receive the light coming from the first optical waveguide layer, a cathode configured to contact with the meshed electro-conductive thin film, an anode having an end to which an electrode plate is connected, a central process control unit configured to control a light quantity of the light source, to process signals sent from the light detector and to control an electric voltage applied between the cathode and the anode, an electric power supply circuit having an electric power-receiving induction coil, a serial port connected to the central process control unit and a data transmission induction coil connected to the serial port, and (b) a charging device comprising an electric power transmission induction coil and a data-receiving induction coil connected with the electric power-receiving induction coil and the data transmission induction coil located in the detection unit electromagnetically, and a microcomputer configured to transfer data received by the data-receiving induction coil to an outside computer.

According to an eighth aspect of the present invention, an optical waveguide system for glucose measurement comprises (a)(1) an optical waveguide device comprising an optical waveguide sensor having a substrate, a first optical waveguide layer formed on a surface of the substrate, an entrance grating and an exit grating contacting with the first optical waveguide layer and being spaced from each other, a second optical waveguide layer located between the entrance grating and the exit grating while being in contact with the first optical waveguide layer, the second optical waveguide layer having a higher refractive index than that of the first optical waveguide layer and a functioning layer containing an enzyme and a coloring reagent formed on the second optical waveguide layer, and (2) a detection unit having a light source configured to emit a light to the first optical waveguide layer, a light detector configured to receive the light coming from the first optical waveguide layer, a cathode configured to contact with the second optical waveguide layer, an anode having an end to which an electrode plate is connected, a central process control unit configured to control a light quantity of the light source, to process signals from the light detector and to control an electric voltage applied between the cathode and the anode, an electric power supply circuit having an electric power-receiving induction coil, a serial port connected to the central process control unit and a data transmission induction coil connected to the serial port, and (b) a charging device comprising an electric power transmission induction coil and a data-receiving induction coil connected with the electric power-receiving induction coil and the data transmission induction coil located in the detection unit electromagnetically, and a microcomputer configured to transfer data received by the data-receiving induction coil to an outside computer.

According to a ninth aspect of the present invention, a method for glucose measurement comprises contacting an upper portion of an electro-conductive body formed on a substrate and connected to a cathode of an electric source with a first portion of an analyte, contacting an electrode plate connected to an anode of the electric source with a second portion of the analyte, generating an electric field between the electro-conductive body and the electrode plate, extracting a body fluid containing glucose from the analyte towards the electro-conductive body, causing a coloring reaction by the glucose on the substrate, irradiating a light from beneath one side of the substrate maintaining a pre-determined incident angle, absorbing the light by the coloring reaction within a second optical waveguide layer on the first optical waveguide layer formed on a surface of the substrate, the second optical waveguide layer having a refractive index higher than that of the first optical waveguide layer and measuring the quantity of an emitted light below the other side of the substrate.

BRIEF DESCRIPTION OF DRAWINGS

FIG. 3 is a sectional view of a measuring method by the optical waveguide type glucose sensor shown in FIG. 1.

FIG. 4 is a sectional view showing an optical waveguide type glucose sensor according to a second embodiment of the present invention.

DETAILED DESCRIPTION OF THE INVENTION

Figure 1:
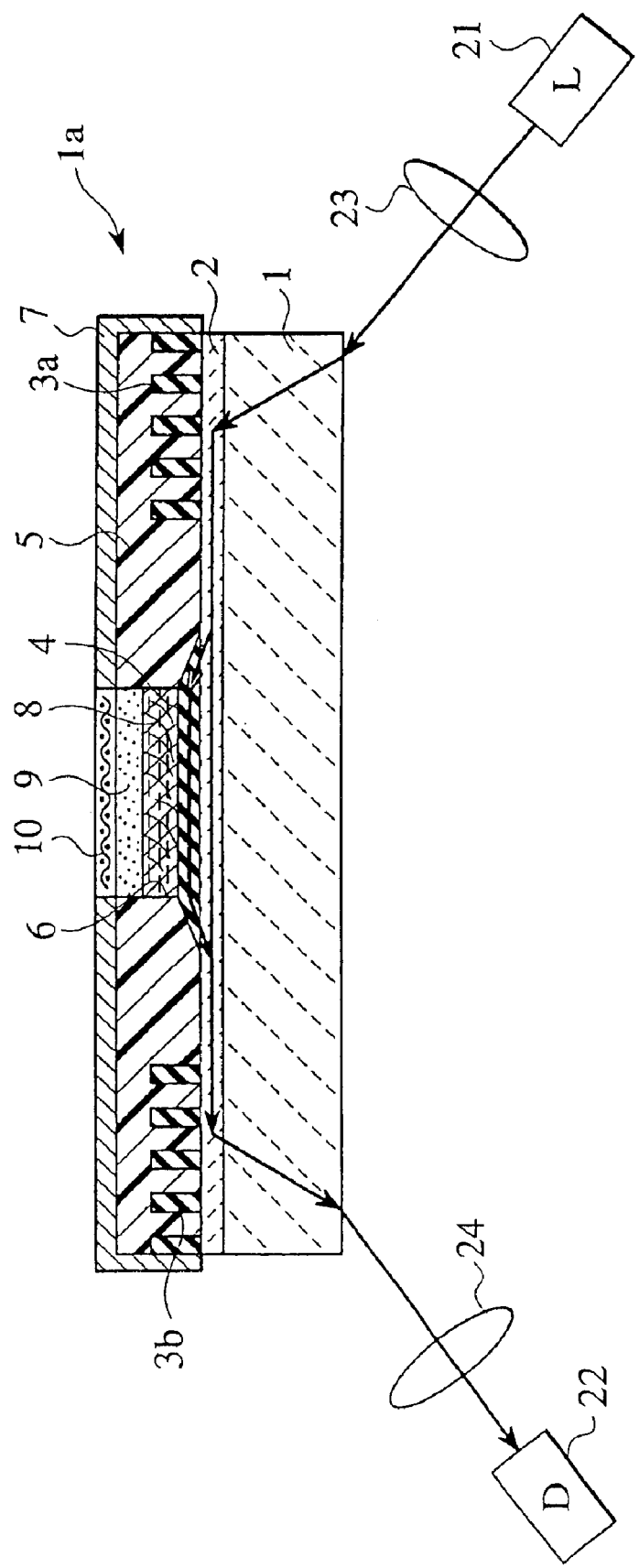
FIG. 1 is a sectional view showing an optical waveguide type glucose sensor according to a first embodiment of the present invention.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

First Embodiment

In an optical waveguide type glucose sensor 1a according to the first embodiment of the present invention, as illustrated in FIG. 1, a substrate 1 which is made of glass, for example, and a first optical waveguide layer 2 having a refractive index higher than that of the substrate 1 and being placed on the surface of the substrate 1, are formed. In addition, a grating 3a located at an entrance portion (hereinafter the entrance grating) and another grating 3b located at an exit portion (hereinafter the exit grating) have refractive indexes higher than that of the first optical waveguide layer 2, and both gratings are respectively formed on the surface in the vicinities of both ends of the first optical waveguide layer 2. Moreover, the second optical waveguide layer 4 in which a circumference is tapered in shape and has a higher refractive index than the first optical waveguide layer 2 and is formed on a part of the first optical waveguide layer 2, is located between the entrance grating 3a and the exit grating 3b.

A protecting layer 5 has a lower refractive index compared to the entrance grating 3a and the exit grating 3b, and is formed on the first optical waveguide layer 2 including an area where the entrance grating 3a and the exit grating 3b are located. A rectangular opening 6 is provided at a part of the protecting layer 5 corresponding to an upper surface of a second optical waveguide layer 4. A stray light trapping layer 7 made of black matrix (a pigment resist), utilized in a liquid crystal display device, for example, is formed on the surface of the protecting layer 5 excluding the inside of the opening 6.

Note that when the refractive index of the substrate 1 is set to be $n_1$, the first optical waveguide layer 2 to be $n_2$, the entrance grating 3a and of the exit grating 3b to be $n_3$, the second optical waveguide layer 4 to be $n_4$, and the protecting layer 5 to be $n_5$, the order of the refractive indexes from largest to smallest is $n_4 \geq n_3 > n_2 > n_1 > n_5$.

A functioning layer 8 containing an enzyme and a coloring reagent is formed on the surface of the second optical waveguide layer 4 exposed through the opening 6. A porous film 9 made of moistened gel, for example, is formed on the functioning layer 8 which is exposed through the opening 6. A meshed electro-conductive thin film 10 to which an electric field (for example, a pulsed electric field) is applied is placed on the porous film 9. The first optical waveguide layer 2 is prepared by ion-exchanging of elements such as K, Na and the like with glass components. A pair of the gratings 3 is prepared by using, for example, titanium oxide ($TiO_2$), zinc oxide (ZnO), lithium niobate ($LiNbO_3$), gallium arsenide (GaAs), indium tin oxide (ITO), tantalum oxide ($Ta_2O_5$) or polyimide. The second optical waveguide layer 4 is prepared by using, for example, $TiO_2$, ZnO, $LiNbO_3$, GaAs, ITO, $Ta_2O_5$ or polyimide. The protecting layer 5 is made of, for example, fluorocarbon resin. Here, for the enzyme to be contained in the functioning layer 8, for example, glucose oxidase as oxidation enzyme, peroxidase as oxidation reduction enzyme, mutarotase used for converting α-D-glucose to β-D-glucose and the like are able to be applied. On the other hand, for the coloring reagent to be contained in the functioning layer 8, for example, dipotassium salt of N, N-bis(2-hydroxy-3-sulfopropyl)tolidine,3,3', 5,5'-tetramethylbenzidine and the like are applicable.

The functioning layer 8 to be listed as examples are, 1) a layer having a structure in which the enzyme and the coloring dyestuff are fixed by cross linking polymers, 2) a layer having a structure in which the enzyme is fixed by lipid molecules having a molecular structure which develops coloring functions against dyestuffs; and the like.

As the cross linking polymer used in the functioning layer 8 written in the above item 1), a polymer having a functional group providing a hydrogen bonding property, for example, photo cross-linking polyvinyl alcohol is listed. As the lipid molecule used in the functioning layer 8 as shown in the item 2) a molecule having a molecular structure which develops the function of coloring dyestuff, a compound of which chemical structure is shown in the chemical structure (1) below, for example, is listed.

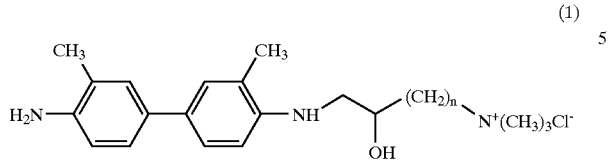

(1)

The meshed electro-conductive thin film 10 is prepared by use of, for example, a thin film of titanium and the like.

Next, an example for a manufacturing method of the optical waveguide type glucose sensor 1a which has been previously described will be explained referencing FIGS. 2A to 2G.

Figure 2A:
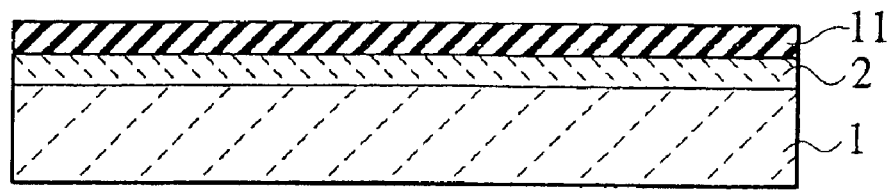
FIGS. 2A–2G are a sectional view of the manufacturing process of the optical waveguide type glucose sensor shown in FIG. 1.

(a) To begin with, as shown in FIG. 2A, the surface of the substrate 1 made of, for example, borosilicate glass, is dipped into an ion-exchanging solution such as potassium nitrate solution at 380° C. through 400° C. to conduct an ion exchange of elements which are high in refractive indexes such as potassium and sodium. Through this process, the first optical waveguide layer 2 is formed. After the process, a layer 11 made of an ingredient of a higher refractive index compared to the first optical waveguide layer 2, such as $TiO_2$, ZnO, $LiNbO_3$, GaAs, ITO, $Ta_2O_5$ and polyimide, is formed by Chemical Vapor Deposition (CVD) method and the like on the first optical waveguide layer 2.

Figure 2B:
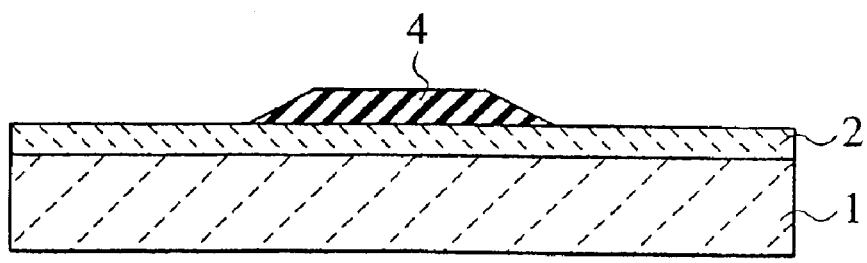

(b) Next, as illustrated in FIG. 2B, the layer 11 having a material with a refractive index higher than that of the first optical waveguide layer 2 is patterned by a photo-etching technique to form the second optical waveguide layer 4, which is in a shape having a tapered circumference, near the center of the first optical waveguide layer 2.

Figure 2C:
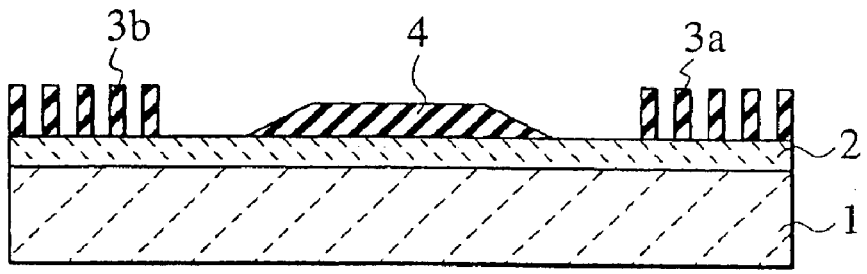

(c) Subsequently, in a similar way to (a) again, another layer of which the refractive index is higher than that of the first optical waveguide layer 2 such as titanium oxide, zinc oxide, lithium niobate and GaAs is formed by CVD method or the like, for example, over the entire surface area. Then, the layer is patterned by a photo-etching technique, thus forming the entrance grating 3a and the exit grating 3b as shown in FIG. 2C in the vicinities of both ends on the surface of the first optical waveguide layer 2.

Figure 2D:
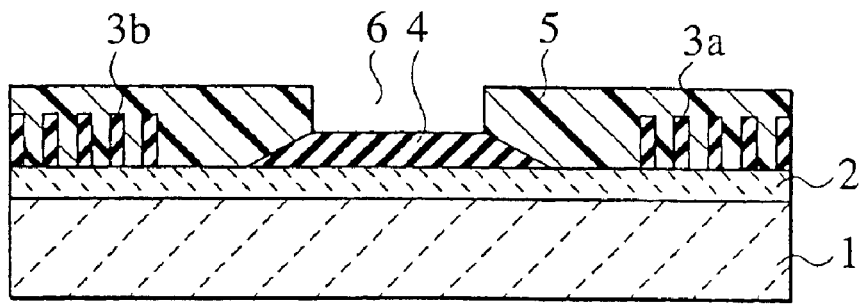

(d) Then, a covering layer made of a material such as photo-sensitive fluorine-based resin, having a lower refractive index compared to that of the entrance grating 3a and the exit grating 3b, is coated upon the first optical waveguide layer 2 including the entrance grating 3a, the exit grating 3b and the second waveguide layer 4. Sequentially, exposure and development processes are conducted against the covering layer. Thus, the protecting layer 5 comprised of a photo-sensitive fluorine-based resin having the rectangular opening 6 which is located in the position corresponding to the surface of the second optical waveguide layer 4 is formed as shown in FIG. 2D.

Figure 2E:
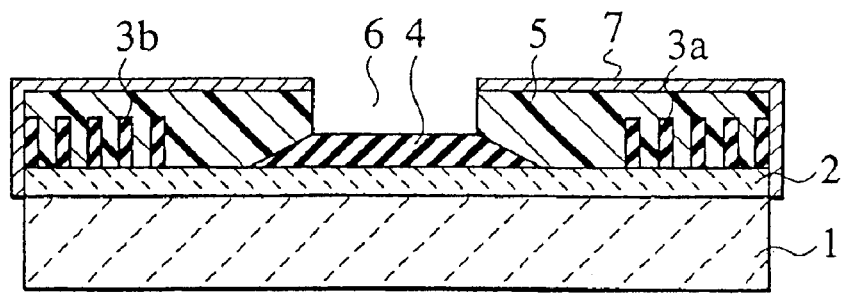

(e) Next, the stray light trapping layer 7 comprised of black matrix, for example, utilized in a liquid crystal display device, is formed on the surface of the protecting layer 5 excluding the inside of the opening 6 by use of CVD method or vacuum deposition as shown in FIG. 2E.

Figure 2F:
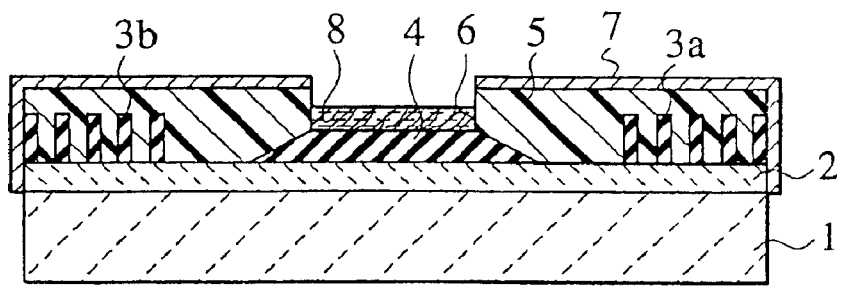

(f) In addition, the functioning layer 8 containing the enzyme and the coloring dyestuff is formed on the surface of the second optical waveguide layer 4 exposed through the opening 6 of the protecting layer 5 as explained in FIG. 2F. More specifically, the methods are, for example, 1) the enzyme and the coloring dyestuff are mixed with cross-linking polymer (for example, photo-soluble polyvinyl alcohol) in the presence of a solvent. The solution is applied on the surface of the second waveguide layer 4 which is exposed through the opening 6 of the protecting layer 5 by use of ink jet or spin coating, followed by light irradiation to conduct cross-linking of photo cross-linking polyvinyl alcohol;

2) a solution containing the enzyme and lipid molecules having a molecular structure to develop the coloring function against the dyestuffs is coated on the surface of the second waveguide layer 4 exposed through the opening 6 of the protecting layer 5 by inkjet,spin coating or the like, and is dried. Thus, the functioning layer 8 containing the enzyme and the coloring dyestuff is formed.

Figure 2G:
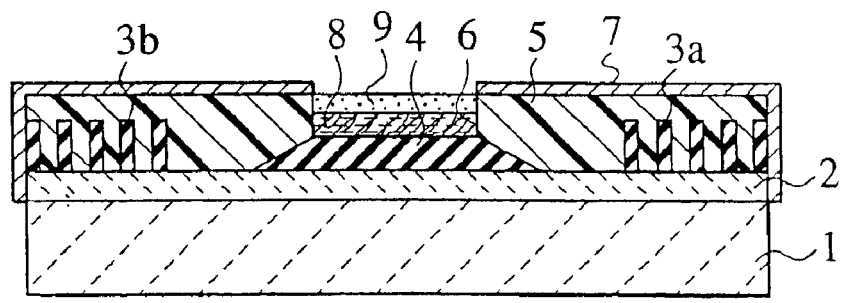

(g) Subsequently, a solution containing, for example, organic monomer, photo-reaction initiator and poor solvent such as methyl decanate is coated, dried and photo-polymerized on the functioning layer 8 exposed through the opening 6 of the protecting layer 5. After the above, through a washing treatment, the porous film 9 is formed as shown in FIG. 2G. Then, the meshed electro-conductive thin film 10 in which an electric field such as a pulsed electric field is applied is placed on the porous film 9 to manufacture the optical waveguide type glucose sensor 1a exhibited in FIG. 1.

Next, a measuring method of glucose in an analyte 100 will be explained using FIG. 3. The cathode of an electric source 102 is wired to the meshed electro-conductive thin film 10, and the anode of the electric source 102 is wired to an electrode plate 101 as shown in FIG. 3. Then, the analyte 100, for example, a part of a human skin, is placed to contact with the portion of the porous film 9 provided on the functioning layer 8 containing the enzyme and the coloring reagent of the optical waveguide type glucose sensor 1a shown in FIG. 1, and, in addition, the electrode plate 101 is brought into contact with another portion of the analyte 100. In this situation, when a desired electric field such as a pulsed electric field is applied from the electric source 102 between the meshed electro-conductive thin film 10 placed on top of the porous film 9 and the electrode plate 101, a body fluid containing glucose is effectively extracted from the analyte 100 to the functioning layer 8 through the porous film 9, in other words, reverse iontophoresis is realized. The glucose within the body fluid generates hydrogen peroxide ($H_2O_2$) through an oxidation enzyme reaction with glucose oxidase (GOD) and the like in the functioning layer 8, followed by the generation of radical oxygen atom (O*) from the hydrogen peroxide through an oxidation-reduction enzyme reaction with peroxidase (POD) and the like. The coloring reagent is colored by the oxygen atom radical. The reactions above are schematically formulated as (2), (3) and (4) below:

glucose+oxidation enzyme(GOD and the like)→$H_2O_2$ (2)

$H_2O_2$+oxidation reduction enzyme (POD and the like)→O* (3)

O*+coloring reagent→coloring (4)

In such a situation, a light source 21 (for example, a semiconductor laser of 650 nm in wave length) and a light detector 22 are respectively positioned at the left-hand side of the back and at the right-hand side of the back of substrate 1 of the optical waveguide type glucose sensor 1a as shown in FIG. 1. Then, a laser light is made incident to the back surface of the substrate 1 of the glucose sensor via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 4 which is higher than the first optical waveguide layer 2 in refractive index. The TM mode laser light transmits in the first optical waveguide layer 2 and the TE mode laser light transmits in the second optical waveguide layer 4. At this point, the intensity of the light transmitting in the second optical waveguide layer 4 directly under the functioning layer 8 changes, due to a change based upon the coloring of the coloring reagent (for example, absorbance change) that occurs in the functioning layer 8. The lights transmitted through the first optical waveguide layer 2 and the second optical waveguide layer 4 recombine and interfere with each other at the boundary face between the first optical waveguide layer 2 and the second optical waveguide layer 4 near the light detector 22. Therefore, the change in the intensity of the light transmitting in the second optical waveguide layer 4 can be amplified. Thus. the detection of even an extremely small change in the light which transmits in the second optical waveguide layer 4 becomes possible at the light detector 22 through the polarizing filter 24, wherein the small change is based on the coloring of the coloring reagent caused by the reaction between glucose of the analyte 100 (under a human skin) and the enzyme in the functioning layer 8.

Therefore, according to the optical waveguide type glucose sensor 1a of the first embodiment having the structure shown in FIG. 1, the following matters are possible. It is possible to effectively extract glucose from the analyte 100 (for example, glucose-containing body fluid located under human skin) to the functioning layer 8. In other words, reverse iontophoresis is possible. In the above procedure, the meshed electro-conductive thin film 10 is placed above the functioning layer 8 which contains the enzyme and the coloring reagent, and a desired electric field (for example, a pulsed electric field) is applied from the electric source 102 between the meshed electro-conductive thin film 10 and the electrode plate 101 by use of the power supply wiring shown in FIG. 3. In addition to the above, it is possible to analyze with high sensitivity an extremely small amount of glucose in an extracted body fluid. The reason thereof is, the optical waveguide consists of the first optical waveguide layer 2 and the second optical waveguide layer 4, and it is possible to detect the fine change in the light transmitting in the second optical waveguide layer 4 at the boundary face between the first optical waveguide layer 2 and the second optical waveguide layer 4, wherein the change of the light is caused by the coloring of the coloring reagent due to the reaction between the glucose extracted from the analyte 100 (under a human skin) and the enzyme in the functioning layer 8.

In addition, as shown in FIG. 1, the protecting layer 5 is formed on the first optical waveguide layer 2 including the entrance grating 3a and the exit grating 3b. Thus, it is possible to prevent external stress from directly affecting to the first optical waveguide layer 2, the entrance grating 3a and exit grating 3b. Because of the above, it is possible to prevent the light transmitting in the first optical waveguide layer 2 from leaking outside, wherein the light leak is caused by the change in the refractive index of the members therein when the first optical waveguide layer 2, the entrance grating 3a and the exit grating 3b are directly pressed on by an external stress. Moreover, due to the fact that the protecting layer 5 is made of a material of which the refractive index is lower than that of the first optical waveguide layer 2, the light transmitting in the first optical waveguide layer 2 is able to be kept inside the first optical waveguide layer 2 by the effective total reflection at the boundary face between the first optical waveguide layer 2 and the protecting layer 5. Thus, it is possible to prevent the light from leaking outside the first optical waveguide layer 2. As a result, an extremely small amount of glucose in the analyte 100 can be analyzed with higher sensitivity.

In addition, the stray light trapping layer 7 is formed on the surface of the protecting layer 5 excluding the inside of the opening 6. Because of this, when the transmitting light in the first optical waveguide layer 2 leaks towards the protecting layer 5 through the boundary face with the protecting layer 5, the leaked light is able to be trapped at the stray light trapping layer 7.

In other words, if the light transmitting in the first optical waveguide layer 2 leaks through the boundary face with the protecting layer 5 towards the protecting layer 5, the leaked light is totally reflected at the surface of the protecting layer 5 to incident to the second optical waveguide layer 4 as stray light, because of the difference between the refractive indexes of the surface of the protecting layer 5 and the surrounding air. This lowers the detection sensitivity of glucose in the analyte 100. On the contrary, since the stray light trapping layer 7 is formed on the surface of the protecting layer 5, the leaked light is not totally reflected at the surface of the protecting layer 5, but is able to be trapped by the stray light trapping layer 7. Accordingly, it is possible to prevent the leaked light from entering the second optical waveguide layer 4 as stray light, thus it is possible to analyze, with higher sensitivity, glucose in the analyte 100.

In addition, the functioning layer 8 containing the enzyme and the coloring reagent is covered by the porous film 9. Due to this, an adverse effect against the functioning layer 8 caused by an impurity which is extracted from the analyte 100 (for example, the body fluid) can be prevented, wherein the example for the impurity other than glucose is protein, blood cells or the like. That is, due to the change based on the coloring reaction of the coloring reagent caused by the enzyme reaction between the enzyme and the glucose in the functioning layer 8, disturbance affecting the change in the intensity of the light transmitting in the second optical waveguide layer 4 directly under the functioning layer 8 can be reduced, and thus it is possible to analyze with even higher sensitivity an extremely small amount of glucose existing in the body fluid which is extracted from the analyte 100.

Second Embodiment

The optical waveguide type glucose sensor 1b illustrated in FIG. 4 has a structure in which an immobilized coloring reagent layer 13 is formed on the second optical waveguide layer 4 and an immobilized enzyme layer 14 is formed on the immobilized coloring reagent layer 13. In short, the optical waveguide type glucose sensor 1b shown in FIG. 4 has a structure in which the functioning layer 8 in the previously mentioned first embodiment is separated into two layers, the immobilized coloring reagent layer 13 and the immobilized enzyme layer 14.

The immobilized coloring reagent layer 13 is formed by fixing the coloring reagent to the surface of the second optical waveguide layer 4 by the application of silane coupling agent or cross-linking polymer, wherein examples of the coloring reagent are dipotassium N. N-bis(2-hydroxy- 3-sulfopropyl)tolidine salt or 3,3',5,5'-tetramethylbenzidine, an example of the silane coupling agent is aminoalkyltrimethoxysilane, and an example of the cross-linking polymer is photo cross-linking polyvinyl alcohol.

The immobilized enzyme layer 14 is formed by the fixation of peroxidase and mutarotase in addition to glucose oxidase, for example, by use of the lipid film such as a compound having a chemical structure shown in the chemical structure (5) written below.

(5)

The electric source 102 is wired to the meshed electro-conductive thin film 10 and the electrode plate 101 as shown in FIG. 3 in the optical waveguide type glucose sensor 1b illustrated in FIG. 4. Then, the analyte 100, for example, a part of a human skin, is placed to contact with the portion of the porous film 9 provided on the immobilized enzyme layer 14 and, in addition, the electrode plate 101 is brought into contact with another portion of the analyte 100. In this situation, when a desired electric field such as a pulsed electric field is applied from the electric source 102 between the meshed electro-conductive thin film 10 placed on top of the porous film 9 and the electrode plate 101, a body fluid containing glucose is effectively extracted from the analyte 100 to the immobilized enzyme layer 14 through the porous film 9, in other words, reverse iontophoresis is realized. The glucose within the body fluid causes the same enzyme reaction as explained in the first embodiment in the immobilized enzyme layer 14, and the coloring reagent of the immobilized coloring reagent layer 13 under the immobilized enzyme layer 14 is colored by the radical oxygen atom generated in this enzyme reaction. In such a situation, a light source 21 (for example, a semiconductor laser of 650 nm in wave length) and a light detector 22 are respectively positioned at the left-hand side of the back and at the right-hand side of the back of substrate 1 of the optical waveguide type glucose sensor 1b as shown in FIG. 4. Then, a laser light is made incident to the back surface of the substrate 1 of the optical waveguide type glucose sensor 1b via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 4 which is higher than the first optical waveguide layer 2 in refractive index. The TM mode laser light transmits in the first optical waveguide layer 2 and the TE mode laser light transmits in the second optical waveguide layer 4. At this point, the intensity of the light transmitting in the second optical waveguide layer 4 directly under the immobilized coloring reagent layer 13 changes due to a change based upon the coloring of the coloring reagent (for example, absorbance change) that occurs in the immobilized coloring reagent layer 13. The lights transmitted through the first optical waveguide layer 2 and the second optical waveguide layer 4 recombine and interfere with each other at the boundary face between the first optical waveguide layer 2 and the second optical waveguide layer 4 near the light detector 22. Therefore, the change in the intensity of the light transmitting in the second optical waveguide layer 4 can be amplified. Thus, the detection of even an extremely small change in the light which transmits in the second optical waveguide layer 4 becomes possible at the light detector 22 through the polarizing filter 24, wherein the small change is based on the coloring of the coloring reagent in the immobilized coloring reagent layer 13 caused by the reaction between the glucose of the analyte 100 (under a human skin) and the enzyme in the immobilized enzyme layer 14.

Therefore, according to the optical waveguide type glucose sensor 1b of the second embodiment having the structure shown in FIG. 4, the following matters are possible. It is possible to effectively extract glucose from the analyte 100 (for example, glucose-containing body fluid located under a human skin) to the immobilized enzyme layer 14. In other words, reverse iontophoresis is possible. In the above procedure, the meshed electro-conductive thin film 10 is placed above the immobilized enzyme layer 14, and a desired electric field (for example, a pulsed electric field) is applied from the electric source 102 between the meshed electro-conductive thin film 10 and the electrode plate 101 by use of the power supply wiring shown in FIG. 3. In addition to the above, it is possible to analyze with high sensitivity an extremely small amount of glucose in an extracted body fluid. The reason thereof is, the optical waveguide consists of the first optical waveguide layer 2 and the second optical waveguide layer 4, and it is possible to detect the fine change of the light transmitting in the second optical waveguide layer 4 at the boundary face between the first optical waveguide layer 2 and the second optical waveguide layer 4, wherein the change of the light is caused by the coloring of the coloring reagent due to the reaction between the glucose extracted from the analyte 100 (under a human skin) and the enzyme in the immobilized enzyme layer 14 and the immobilized coloring reagent layer 13.

Third Embodiment

Figure 5:
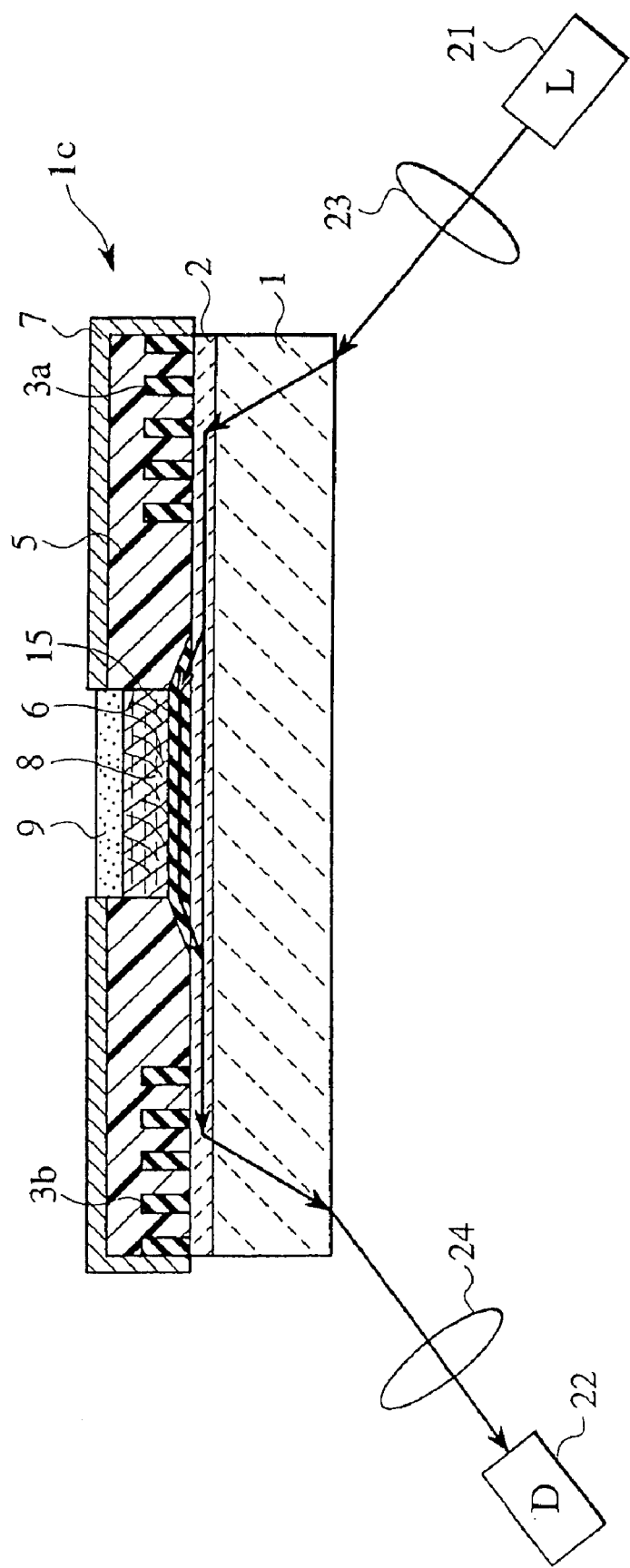
FIG. 5 is a sectional view showing an optical waveguide type glucose sensor according to a third embodiment of the present invention.

An optical waveguide type glucose sensor 1c illustrated in FIG. 5 has a second optical waveguide layer 15 on the first optical waveguide layer 2 between the entrance grating 3a and the exit grating 3b. The second optical waveguide layer 15 is formed by an electro-conductive material having a refractive index higher than that of the first optical waveguide layer 2 such as stannum oxide ($SnO_2$) and ITO, and a desired electric field (for example, a pulsed electric field) is applied to the second optical waveguide layer 15.

As a modification of wiring shown in FIG. 3, the cathode of an electric source 102 is wired to the second optical waveguide layer 15, and the anode of the electric source 102 is wired to an electrode plate 101 in the optical waveguide type glucose sensor 1c illustrated in FIG. 5. Then, the analyte 100, for example, a part of a human skin, is placed to contact with the portion of the porous film 9 provided on the functioning layer 8 containing the enzyme and the coloring reagent, and, in addition, the electrode plate 101 is brought into contact with another portion of the analyte 100. In this situation, when the desired electric field (for example, a pulsed electric field) is applied from the electric source 102 between the second optical waveguide layer 15 formed by the electro-conductive material placed under the porous film 9 and the electrode plate 101, a body fluid containing glucose under the human skin is effectively extracted to the functioning layer 8 through the porous film 9, in other words, reverse iontophoresis is realized. The glucose within the body fluid carries out an enzyme reaction with the enzymes in the functioning layer 8, and the coloring reagent in the functioning layer 8 is colored by the radical oxygen atom generated in the enzyme reaction.

In such a situation, a light source 21 (for example, a semiconductor laser of 650 nm in wave length) and a light detector 22 are respectively positioned at the left-hand side of the back and at the right-hand side of the back of substrate 1 of the optical waveguide type glucose sensor 1c as shown in FIG. 5. Then, a laser light is made incident to the back surface of the substrate 1 of the optical waveguide type glucose sensor 1c via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 15 which is higher than the first optical waveguide layer 2 in refractive index. The TM mode laser light transmits in the first optical waveguide layer 2 and the TE mode laser light transmits in the second optical waveguide layer 15. At this point, the intensity of the light transmitting in the second optical waveguide layer 15 directly under the functioning layer 8 changes due to a change based upon the coloring of the coloring reagent (for example, absorbance change) that occurs in the functioning layer 8. The lights transmitted through the first optical waveguide layer 2 and the second optical waveguide layer 15 recombine and interfere with each other at the boundary face between the first optical waveguide layer 2 and the second optical waveguide layer 15 near the light detector 22. Therefore, the change in the intensity of the light transmitting in the second optical waveguide layer 15 can be amplified. Thus, the detection of even an extremely small change in the light which transmits in the second optical waveguide layer 15 becomes possible at the light detector 22 through the polarizing filter 24, wherein the small change is based on the coloring of the coloring reagent caused by the reaction between the glucose of the analyte 100 (under a human skin) and the enzyme in the functioning layer 8.

Therefore, according to the optical waveguide type glucose sensor 1c of the third embodiment having the structure shown in FIG. 5, it is possible to effectively extract glucose from the analyte 100 (for example, glucose-containing body fluid under a human skin) to the functioning layer 8 by means of applying the desired pulsed electric field between the second optical waveguide layer 15 made of the electro-conductive material under the functioning layer 8 and the electrode plate 101 from the electric source 102 by use of the power supply wiring described above. In other words, reverse iontophoresis is possible. In addition to the above, it is possible to analyze with high sensitivity an extremely small amount of glucose in an extracted body fluid. The reason thereof is, the optical waveguide consists of the first optical waveguide layer 2 and the second optical waveguide layer 15, and it is possible to detect the fine change of the light transmitting in the second optical waveguide layer 15 at the boundary face between the first optical waveguide layer 2 and the second optical waveguide layer 15, wherein the change of the light is caused by the coloring of the coloring reagent due to the reaction between the glucose extracted from the analyte 100 (under a human skin) and the enzyme in the functioning layer 8.

Fourth Embodiment

Figure 6:
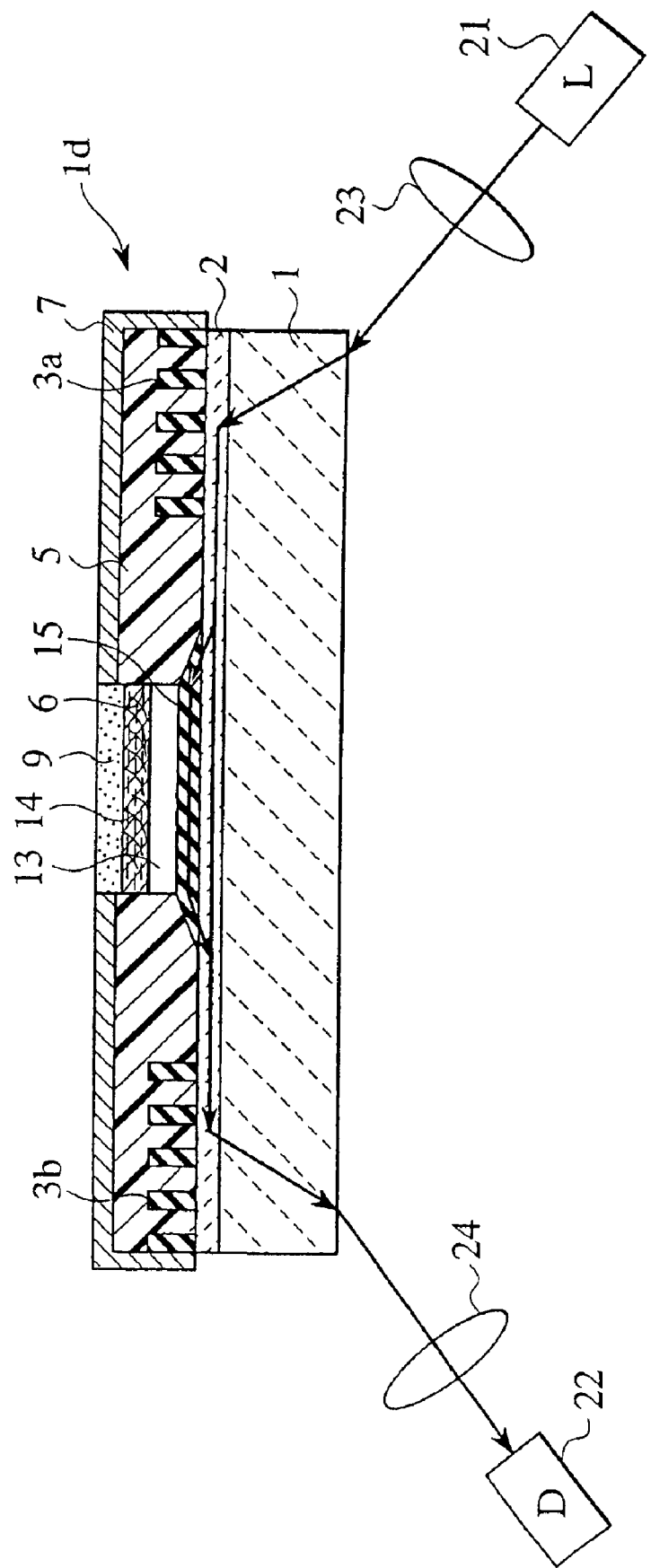
FIG. 6 is a sectional view showing an optical waveguide type glucose sensor according to a fourth embodiment of the present invention.

An optical waveguide type glucose sensor 1d illustrated in FIG. 6 has a second optical waveguide layer 15 on the first optical waveguide layer 2 between the entrance grating 3a and the exit grating 3b, an immobilized coloring reagent layer 13 on the second optical waveguide layer 15 as described in the second embodiment and an immobilized enzyme layer 14 on the immobilized coloring reagent layer 13 as described in the second embodiment. The second optical waveguide layer 15 is formed by an electro-conductive material having a refractive index higher than that of the first optical waveguide layer 2 such as $SnO_2$ and ITO. The functioning layer 8 described in the third embodiment is divided into two layers, that is, the immobilized coloring reagent layer 13 and the immobilized enzyme layer 14 in the optical waveguide type glucose sensor 1d illustrated in FIG. 6, and a desired electric field (for example, a pulsed electric field) is applied to the second optical waveguide layer 15.

As a modification of the wiring shown in FIG. 3, the cathode of an electric source 102 is wired to the second optical waveguide layer 15, and the anode of the electric source 102 is wired to an electrode plate 101 in the optical waveguide type glucose sensor 1d illustrated in FIG. 6. Then, the analyte 100, for example, a part of a human skin, is placed in contact with the portion of the porous film 9 provided on the immobilized enzyme layer 14, and, in addition, the electrode plate 101 is brought into contact with another portion of the analyte 100. In this situation, when the desired electric field (for example, a pulsed electric field) is applied from the electric source 102 between the second optical waveguide layer 15 formed by the electro-conductive material placed under the porous film 9 and the electrode plate 101, a body fluid containing glucose under the human skin is effectively extracted to the immobilized enzyme layer 14 through the porous film 9, in other words, reverse iontophoresis is realized. The glucose within the body fluid carries out an enzyme reaction with the enzymes in the immobilized enzyme layer 14, and the coloring reagent in the immobilized coloring reagent layer 13 directly under the immobilized enzyme layer 14 is colored by the radical oxygen atom generated in the enzyme reaction. In such a situation, a light source 21 (for example, a semiconductor laser of 650 nm in wave length) and a light detector 22 are respectively positioned at the left-hand side of the back and at the right-hand side of the back of the substrate 1 of the optical waveguide type glucose sensor 1d as shown in FIG. 6. Then, a laser light is made incident to the back surface of the substrate 1 of the optical waveguide type glucose sensor 1d via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 15 which is higher than the first optical waveguide layer 2 in refractive index. The TM mode laser light transmits in the first optical waveguide layer 2, and the TE mode laser light transmits in the second optical waveguide layer 15. At this point, the intensity of the light transmitting in the second optical waveguide layer 15 directly under the immobilized coloring reagent layer 13 changes due to a change based upon the coloring of the coloring reagent (for example, absorbance change) that occurs in the immobilized coloring reagent layer 13. The lights transmitted through the first optical waveguide layer 2 and the second optical waveguide layer 15 recombine and interfere with each other at the boundary face between the first optical waveguide layer 2 and the second optical waveguide layer 15 near the light detector 22. Therefore, the change in the intensity of the light transmitting in the second optical waveguide layer 15 can be amplified. Thus, the detection of even an extremely small change in the light which transmits in the second optical waveguide layer 15 becomes possible at the light detector 22 through the polarizing filter 24, wherein the small change is based on the coloring of the coloring reagent in the immobilized coloring reagent layer 13 caused by the reaction between the glucose of the analyte 100 (under a human skin) and the enzyme in the immobilized enzyme layer 14.

Therefore, according to the optical waveguide type glucose sensor 1d of the fourth embodiment having the structure shown in FIG. 6, it is possible to effectively extract glucose from the analyte 100 (for example, glucose-containing body fluid under a human skin) to the functioning layer 8 by means of applying the desired pulsed electric field between the second optical waveguide layer 15 made of the electro-conductive material under the immobilized enzyme layer 14 and the electrode plate 101 from the electric source 102 by use of the power supply wiring described above. In other words, reverse iontophoresis is possible. In addition to the above, it is possible to analyze with high sensitivity an extremely small amount of glucose in an extracted body fluid. The reason thereof is, the optical waveguide consists of the first optical waveguide layer 2 and the second optical waveguide layer 15, and it is possible to detect the fine change of the light transmitting in the second optical waveguide layer 15 at the boundary face between the first optical waveguide layer 2 and the second optical waveguide layer 15, wherein the change of the light is caused by the coloring of the coloring reagent due to the reaction between the glucose extracted from the analyte 100 (under a human skin) and the enzyme in the immobilized enzyme layer 14 and the immobilized coloring reagent layer 13.

Fifth Embodiment

Figure 7:
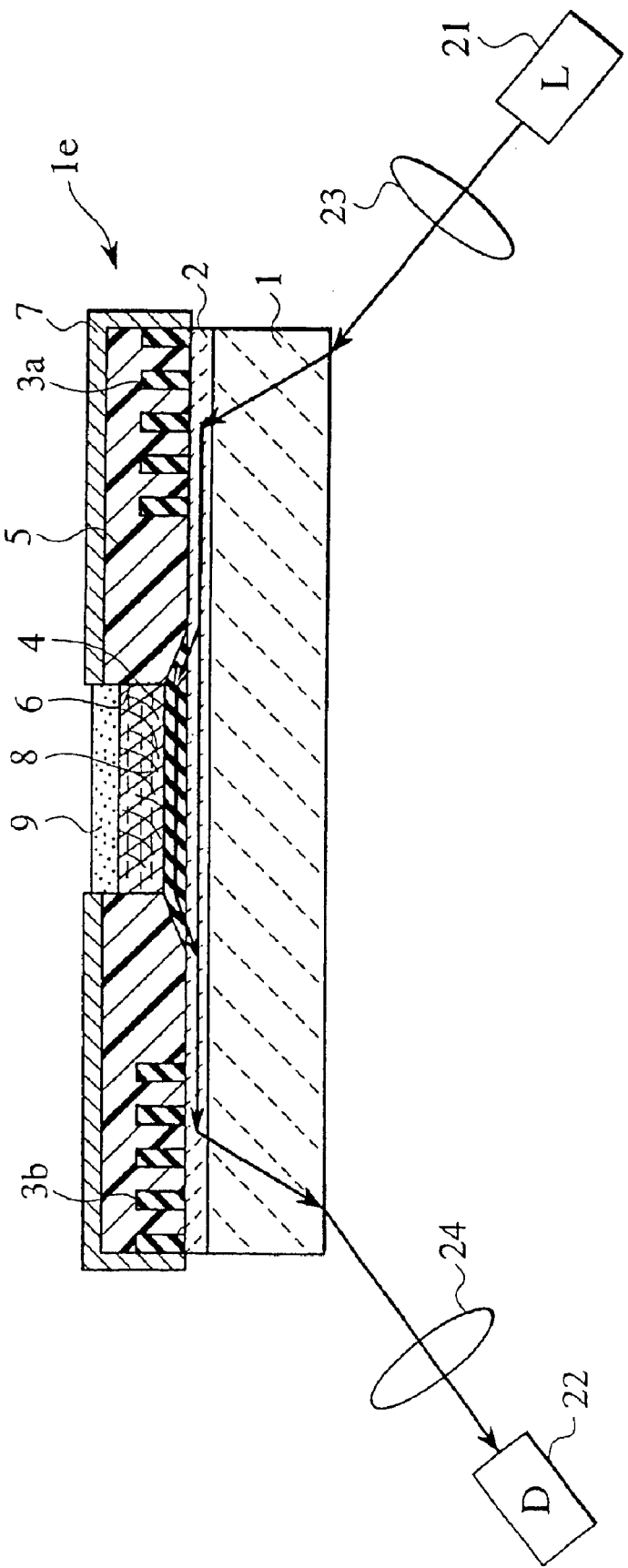
FIG. 7 is a sectional view showing an optical waveguide type glucose sensor according to a fifth embodiment of the present invention.

An optical waveguide type glucose sensor 1e as shown in FIG. 7 is different from the optical waveguide type glucose sensor 1c in the third embodiment as shown in FIG. 5. A second optical waveguide layer 4 on the first optical waveguide layer 2 is formed by a material having a refractive index higher than that of the first optical waveguide layer 2, but it may not be electro-conductive. Other structures are the same as the optical waveguide type glucose sensor 1c in the third embodiment.

A solution containing a glucose such as blood, body fluid and the like is dropped onto a porous film 9 on a functioning layer 8 containing enzymes and a coloring reagent in the optical waveguide type glucose sensor 1e as shown in FIG. 7. The glucose in the solution carries out an enzyme reaction with the enzymes in the functioning layer 8 as described in the first embodiment, and the coloring reagent in the functioning layer 8 is colored by the radical oxygen atom generated in the enzyme reaction. In such a situation, a light source 21 (for example, a semiconductor laser of 650 nm in wave length) and a light detector 22 are respectively positioned at the left-hand side of the back and at the right-hand side of the back of the substrate 1 of the optical waveguide type glucose sensor 1e as shown in FIG. 7. Then, a laser light is made incident to the back surface of the substrate 1 of the optical waveguide type glucose sensor 1e via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 4 which is higher than the first optical waveguide layer 2 in refractive index. The TM mode laser light transmits in the first optical waveguide layer 2 and the TE mode laser light transmits in the second optical waveguide layer 4. At this point, the intensity of the light transmitting in the second optical waveguide layer 4 directly under the functioning layer 8 changes due to a change based upon the coloring of the coloring reagent (for example, absorbance change) that occurs in the functioning layer 8. The lights transmitted through the first optical waveguide layer 2 and the second optical waveguide layer 4 recombine and interfere with each other at the boundary face between the first optical waveguide layer 2 and the second optical waveguide layer 4 near the light detector 22. Therefore, the change in the intensity of the light transmitting in the second optical waveguide layer 4 can be amplified. Thus, the detection of even an extremely small change in the light which transmits in the second optical waveguide layer 4 becomes possible at the light detector 22 through the polarizing filter 24, wherein the small change is based on the coloring of the coloring reagent caused by the reaction between the glucose in the solution and the enzyme in the functioning layer 8.

Therefore, according to the optical waveguide type glucose sensor 1e of the fifth embodiment having the structure shown in FIG. 7, it is possible to analyze with high sensitivity an extremely small amount of glucose in the solution. The reason thereof is, the optical waveguide consists of the first optical waveguide layer 2 and the second optical waveguide layer 4, and it is possible to detect the fine change of the light transmitting in the second optical waveguide layer 4 at the boundary face between the first optical waveguide layer 2 and the second optical waveguide layer 4, wherein the change of the light is caused by the coloring of the coloring reagent due to the reaction between the glucose in the solution and the enzyme in the functioning layer 8.

Sixth Embodiment

Figure 8:
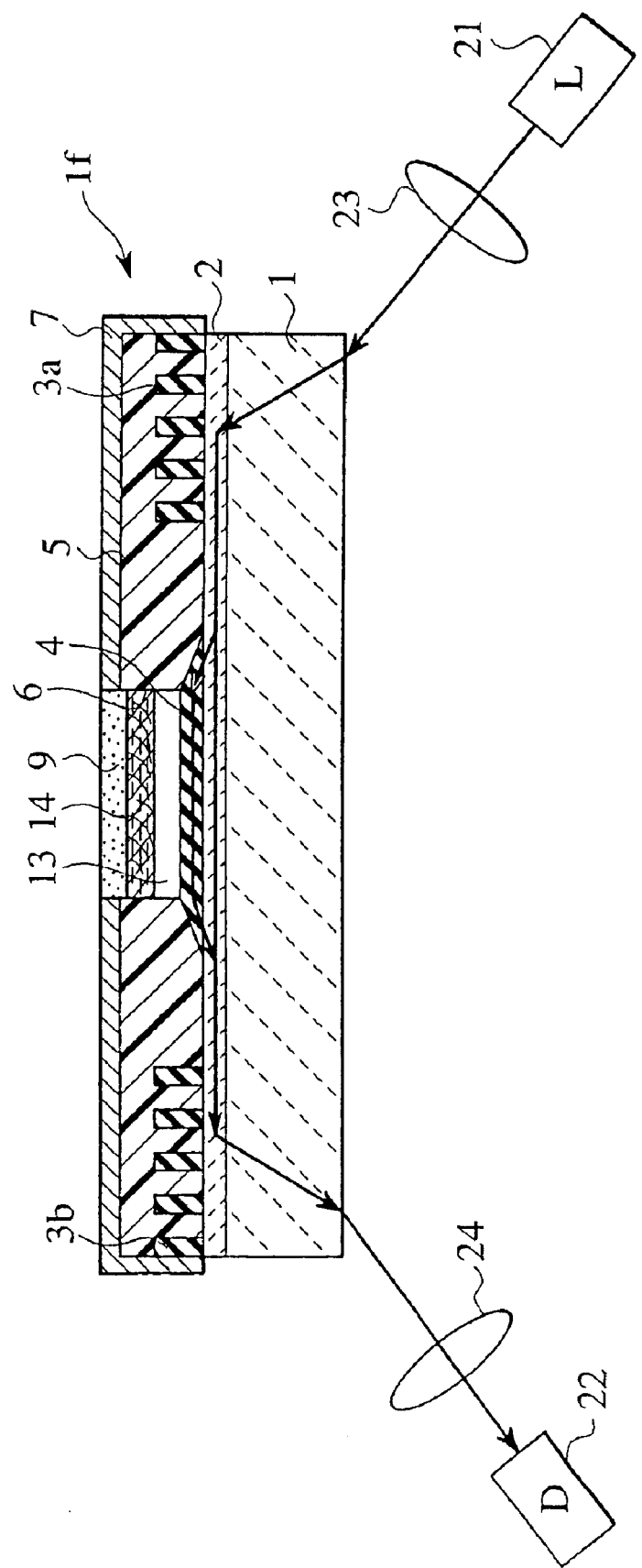
FIG. 8 is a sectional view showing an optical waveguide type glucose sensor according to a sixth embodiment of the present invention.

An optical waveguide type glucose sensor 1f as shown in FIG. 8 is different from the optical waveguide type glucose sensor 1d in the fourth embodiment as shown in FIG. 6. A second optical waveguide layer 4 on a first optical waveguide layer 2 is formed by a material having a refractive index higher than that of the first optical waveguide layer 2, but it may not be electro-conductive. Other structures are same as the optical waveguide type glucose sensor 1d in the fourth embodiment.

A solution containing a glucose such as blood, body fluid and the like is dropped onto a porous film 9 on an immobilized enzyme layer 14 containing enzymes in the optical waveguide type glucose sensor 1e as shown in FIG. 8. The glucose in the solution carries out an enzyme reaction with the enzymes in the immobilized enzyme layer 14, and the coloring reagent in an immobilized coloring reagent layer 13 directly under the immobilized enzyme layer 14 is colored by the radical oxygen atom generated in the enzyme reaction. In such a situation, a light source 21 (for example, a semiconductor laser of 650 nm in wave length) and a light detector 22 are respectively positioned at the left-hand side of the back and at the right-hand side of the back of the substrate 1 of the optical waveguide type glucose sensor 1f as shown in FIG. 8. Then, a laser light is made incident to the back surface of the substrate 1 of the optical waveguide type glucose sensor 1f via a polarizing filter 23 from the light source 21. The laser light goes through the substrate 1, is deflected at the boundary face between the entrance grating 3a and the first optical waveguide layer 2, and transmits inside the first optical waveguide layer 2. The laser light transmitted through the first optical waveguide layer 2 is divided into two modes (TM mode and TE mode) at the boundary face with the second optical waveguide layer 4 which is higher than the first optical waveguide layer 2 in refractive index. The TM mode laser light transmits in the first optical waveguide layer 2 and the TE mode laser light transmits in the second optical waveguide layer 4. At this point, the intensity of the light transmitting in the second optical waveguide layer 4 directly under the immobilized coloring reagent layer 13 changes due to a change based upon the coloring of the coloring reagent (for example, absorbance change) that occurs in the immobilized coloring reagent layer 13. The lights transmitted through the first optical waveguide layer 2 and the second optical waveguide layer 4 recombine and interfere with each other at the boundary face between the first optical waveguide layer 2 and the second optical waveguide layer 4 near the light detector 22. Therefore, the change in the intensity of the light transmitting in the second optical waveguide layer 4 can be amplified. Thus, the detection of even an extremely small change in the light which transmits in the second optical waveguide layer 4 becomes possible at the light detector 22 through the polarizing filter 24, wherein the small change is based on the coloring of the coloring reagent in the immobilized coloring reagent layer 13 caused by the reaction between the glucose in the solution and the enzyme in the immobilized enzyme layer 14.

Therefore, according to the optical waveguide type glucose sensor 1f of the sixth embodiment having the structure shown in FIG. 8, it is possible to analyze with high sensitivity an extremely small amount of glucose in the solution. The reason thereof is, the optical waveguide consists of the first optical waveguide layer 2 and the second optical waveguide layer 4, and it is possible to detect the fine change of the light transmitting in the second optical waveguide layer 4 at the boundary face between the first optical waveguide layer 2 and the second optical waveguide layer 4, wherein the change of the light is caused by the coloring of the coloring reagent due to the reaction between the glucose in the solution and the enzyme in the immobilized enzyme layer 14 and the immobilized coloring reagent layer 13.

Seventh Embodiment

Figure 9:
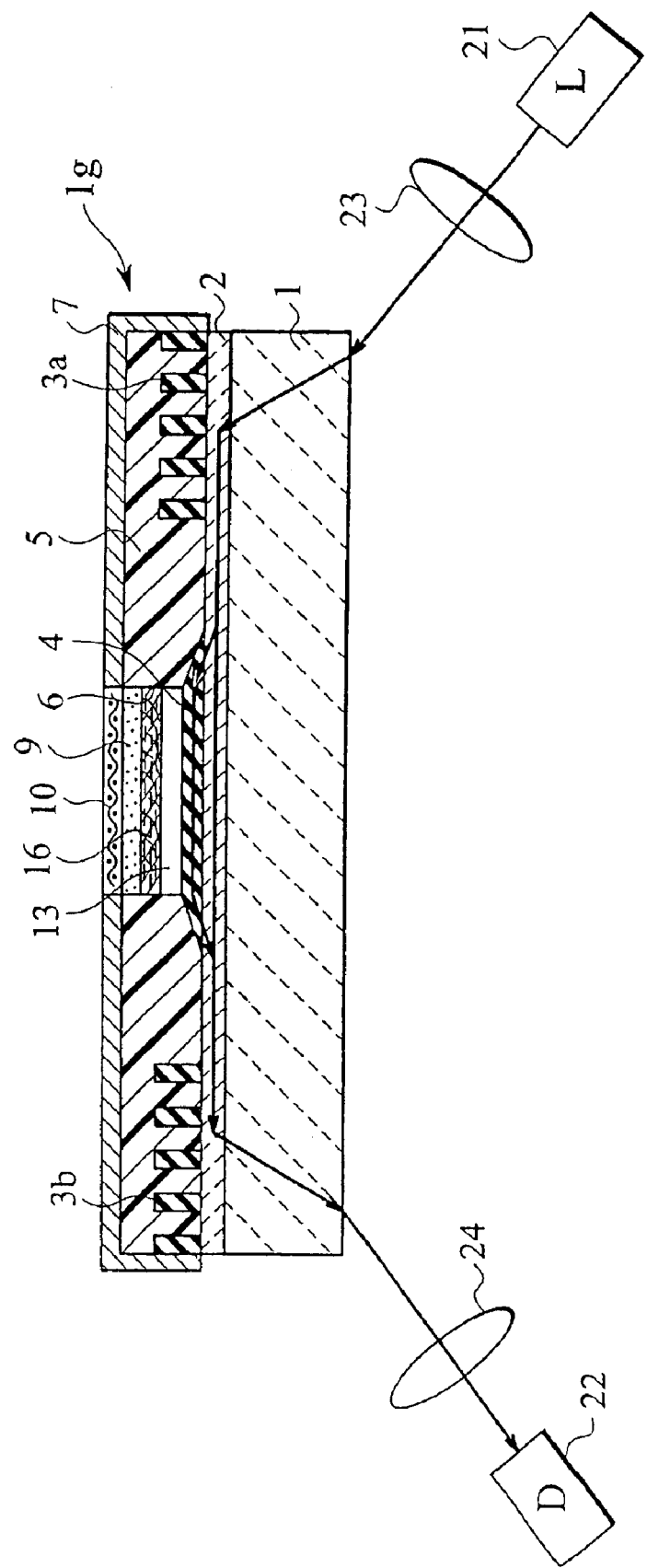
FIG. 9 is a sectional view showing an optical waveguide type glucose sensor according to a seventh embodiment of the present invention.

The optical waveguide type glucose sensor 1g illustrated in FIG. 9 has a structure in which an immobilized coloring reagent layer 13 is formed on a second optical waveguide layer 4 and an immobilized enzyme-catalyst layer 16 is formed on the immobilized coloring reagent layer 13. In short, the optical waveguide type glucose sensor 1g shown in FIG. 9 has a structure in which the functioning layer 8 in the first embodiment mentioned is separated into two layers, the immobilized coloring reagent layer 13 and the immobilized enzyme-catalyst layer 16.

The immobilized coloring reagent layer 13 is formed by fixing the coloring reagent to the surface of the second optical waveguide layer 4 by the application of a silane coupling agent or cross-linking polymer, wherein examples of the coloring reagent are dipotassium N,N-bis(2-hydroxy-3-sulfopropyl)tolidine salt or 3,3',5,5'-tetramethylbenzidine, an example of the silane coupling agent is aminoalkyltrimethoxysilane, and an example of the cross-linking polymer is photo cross-linking polyvinyl alcohol.

The immobilized enzyme-catalyst layer 16 is formed by mixing a glucose oxidase and platinum (Pt) in a water content gel. The difference between the immobilized enzyme-catalyst layer 16 and the immobilized enzyme layer 14 described before is to contain the platinum in place of enzymes such as a peroxidase and the like in order to generate a radical oxygen atom by using a metal catalyst, instead of the reaction of enzymes such as the peroxidase and the like.

An electric source 102 is wired to a meshed electro-conductive thin film 10 and to an electrode plate 101 as shown in FIG. 3 in the optical waveguide type glucose sensor 1g shown in FIG. 9. Then, the analyte 100, for example, a part of a human skin, is placed to contact with a portion of the porous film 9 provided on the immobilized enzyme-catalyst layer 16, and, in addition, the electrode plate 101 is brought into contact with another portion of the analyte 100. In this situation, when a desired electric field (for example, a pulsed electric field) is applied from the electric source 102 between the meshed electro-conductive thin film 10 placed on top of the porous film and the electrode plate 101, a body fluid containing glucose is effectively extracted from the analyte 100 to the immobilized enzyme-catalyst layer 16 through the porous film 9, in other words, reverse iontophoresis is realized. The glucose within the body fluid generates hydrogen peroxide ($H_2O_2$) through an enzyme reaction with glucose oxidase. Then a radical oxygen atom ($O^*$) is generated by catalytic activity of the platinum. The coloring reagent is colored by the oxygen atom radical in the immobilized coloring reagent layer 13 directly under the immobilized enzyme-catalyst layer 16. In short, the reaction (3) of schematically formulated (2)~(4) in the first embodiment is replaced by (6) below:

$$H_2O_2 + Pt \rightarrow O^* \qquad (6)$$

A measuring method of glucose is the same as the one in the second embodiment. The detection of even an extremely small change in the light which transmits in the second optical waveguide layer 4 becomes possible at the light detector 22 through the polarizing filter 24, wherein the small change is based on the coloring of the coloring reagent in the immobilized coloring reagent layer 13.

Therefore, according to the optical waveguide type glucose sensor 1g of the seventh embodiment having the structure shown in FIG. 9, the following matters are possible. It is possible to effectively extract glucose from the analyte 100 (for example, glucose-containing body fluid located under a human skin) to the immobilized enzyme-catalyst layer 16. In other words, reverse iontophoresis is possible. In the above procedure, the meshed electro-conductive thin film 10 is placed above the immobilized enzyme-catalyst layer 16, and a desired electric field (for example, a pulsed electric field) is applied from the electric source 102 between the meshed electro-conductive thin film 10 and the electrode plate 101 by use of the power supply wiring shown in FIG. 3. In addition to the above, it is possible to analyze with high sensitivity an extremely small amount of glucose in an extracted body fluid. The reason thereof is, the optical waveguide consists of the first optical waveguide layer 2 and the second optical waveguide layer 4, and it is possible to detect the fine change of the light transmitting in the second optical waveguide layer 4 at the boundary face between the first optical waveguide layer 2 and the second optical waveguide layer 4, wherein the change of the light is caused by the coloring of the coloring reagent due to the reaction between the glucose extracted from the analyte 100 (under a human skin) and the enzyme in the immobilized enzyme-catalyst layer 16 and the immobilized coloring reagent layer 13.

Eighth Embodiment

Figure 10:
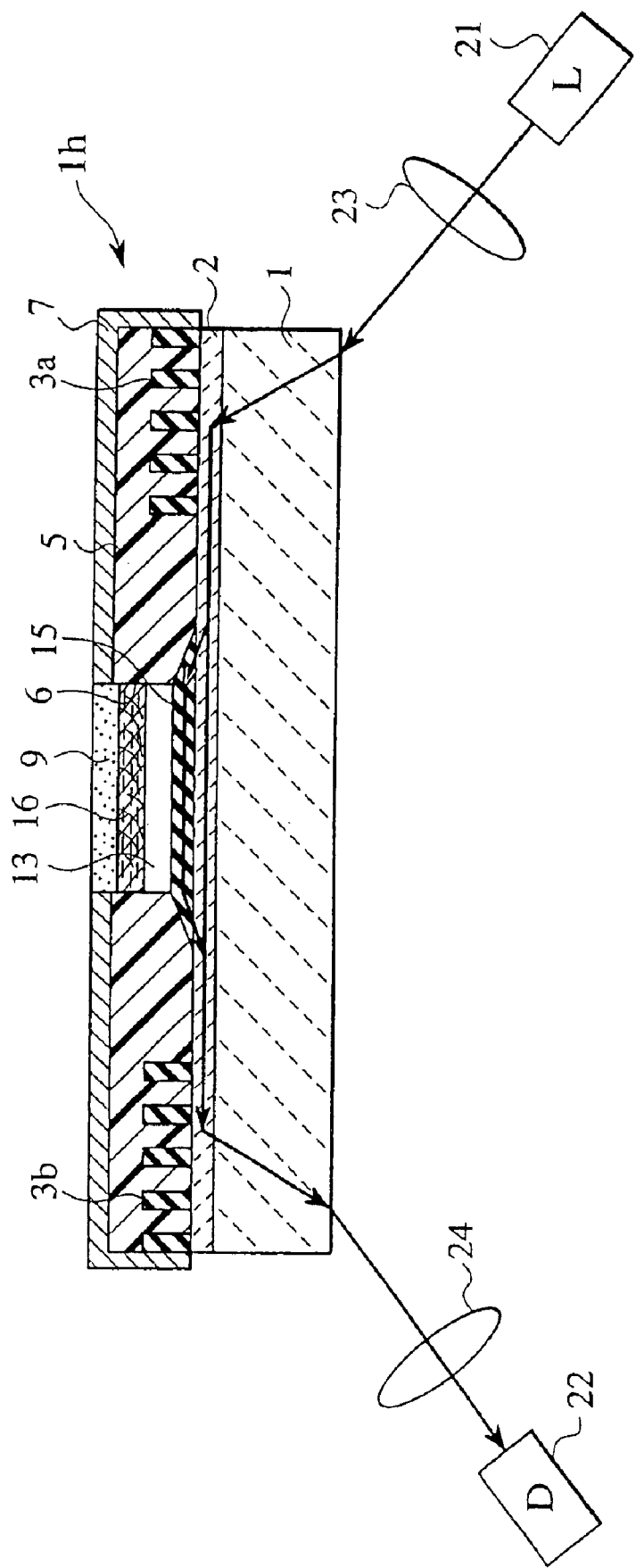
FIG. 10 is a sectional view showing an optical waveguide type glucose sensor according to an eighth embodiment of the present invention.

An optical waveguide type glucose sensor 1h illustrated in FIG. 10 has a second optical waveguide layer 15 on the first optical waveguide layer 2 between the entrance grating 3a and the exit grating 3b, an immobilized coloring reagent layer 13 on the second optical waveguide layer 15 as described in the seventh embodiment and an immobilized enzyme-catalyst layer 16 on the immobilized coloring reagent layer 13 as described in the seventh embodiment. The second optical waveguide layer 15 is formed by an electro-conductive material such as $SnO_2$ and ITO having a refractive index higher than that of the first optical waveguide layer 2. The functioning layer 8 described in the third embodiment is divided into two layers, that is, the immobilized coloring reagent layer 13 and the immobilized enzyme-catalyst layer 16 in the optical waveguide type glucose sensor 1h illustrated in FIG. 10, and a desired electric field (for example, a pulsed electric field) is applied to the second optical waveguide layer 15.

As a modification of wiring shown in FIG. 3, the cathode of an electric source 102 is wired to the second optical waveguide layer 15, and the anode of the electric source 102 is wired to an electrode plate 101 in the optical waveguide type glucose sensor 1h illustrated in FIG. 10. Then, the analyte 100, for example, a part of a human skin, is placed in contact with a portion of the porous film 9 provided on the immobilized enzyme-catalyst layer 16, and, in addition, the electrode plate 101 is brought into contact with another portion of the analyte 100. In this situation, when the desired electric field (for example, the pulsed electric field) is applied from the electric source 102 between the second optical waveguide layer 15 formed by the electro-conductive material placed under the porous film 9 and the electrode plate 101, a body fluid containing glucose under the human skin is effectively extracted to the immobilized enzyme-catalyst layer 16 through the porous film 9, in other words, reverse iontophoresis is realized. The glucose within the body fluid generates hydrogen peroxide ($H_2O_2$) through an enzyme reaction with glucose oxidase. Then a radical oxygen atom (O*) is generated from the hydrogen peroxide by catalytic activity of the platinum. The coloring reagent is colored by the radical oxygen atom in the immobilized coloring reagent layer 13 directly under the immobilized enzyme-catalyst layer 16.

A measuring method of glucose is the same as the one in the fourth embodiment. The detection of even an extremely small change in the light which transmits in the second optical waveguide layer 15 becomes possible at the light detector 22 through the polarizing filter 24, wherein the small change is based on the coloring of the coloring reagent in the immobilized coloring reagent layer 13.

Therefore, according to the optical waveguide type glucose sensor 1h of the eighth embodiment having the structure shown in FIG. 10, it is possible to effectively extract glucose from the analyte 100 (for example, glucose-containing body fluid under a human skin) to the immobilized enzyme-catalyst layer 16 by means of applying the desired pulsed electric field between the second optical waveguide layer 15 made of the electro-conductive material under the immobilized enzyme-catalyst layer and the electrode plate 101 from the electric source by use of the power supply wiring described above. In other words, reverse iontophoresis is possible. In addition to the above, it is possible to analyze with high sensitivity an extremely small amount of glucose in an extracted body fluid. The reason thereof is, the optical waveguide consists of the first optical waveguide layer 2 and the second optical waveguide layer 15, and it is possible to detect the fine change of the light transmitting in the second optical waveguide layer 15 at the boundary face between the first optical waveguide layer 2 and the second optical waveguide layer 15, wherein the change of the light is caused by the coloring of the coloring reagent due to the reaction between the glucose extracted from the analyte 100 (under a human skin) and the enzyme in the immobilized enzyme-catalyst layer 16 and the immobilized coloring reagent layer 13.

Ninth Embodiment

Figure 11:
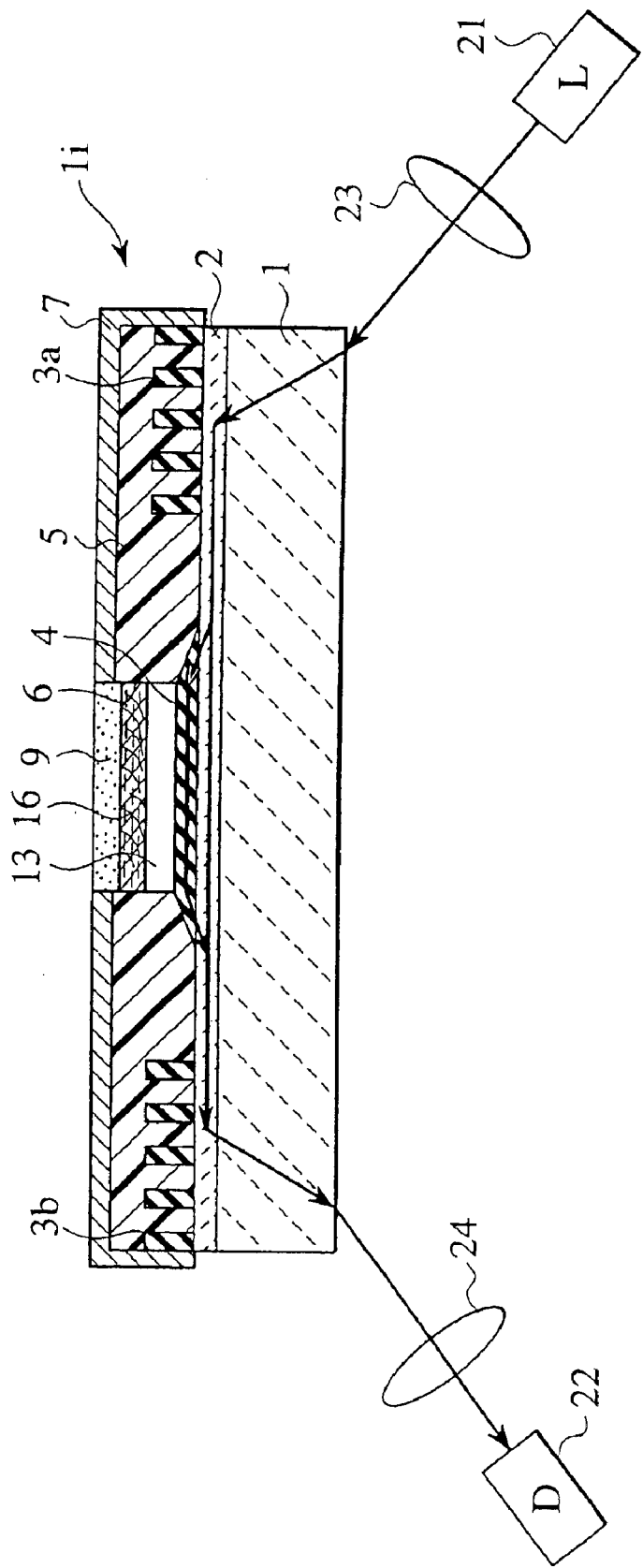
FIG. 11 is a sectional view showing an optical waveguide type glucose sensor according to a ninth embodiment of the present invention.

An optical waveguide type glucose sensor 1i shown in FIG. 11 is different from the optical waveguide type glucose sensor 1h of the eighth embodiment shown in FIG. 10. A second optical waveguide layer 4 on a first optical waveguide layer 2 is formed by a material having a refractive index higher than that of the first optical waveguide layer 2, but it may not be electro-conductive. Other structures are the same as the optical waveguide type glucose sensor in the eighth embodiment.

A solution containing a glucose such as blood, body fluid and the like is dropped onto a porous film 9 on an immobilized enzyme-catalyst layer 16 in the optical waveguide type glucose sensor 1i as shown in FIG. 11. The glucose in the solution generates hydrogen peroxide ($H_2O_2$) through an enzyme reaction with glucose oxidase in the immobilized enzyme-catalyst layer 16. Then a radical oxygen atom (O*) is generated from the hydrogen peroxide by catalytic activity of the platinum. The coloring reagent is colored by the radical oxygen atom in the immobilized coloring reagent layer 13 directly under the immobilized enzyme-catalyst layer 16.

A method of measuring glucose is the same as the one in the fourth embodiment. The detection of even an extremely small change in the light which transmits in the second optical waveguide layer 4 becomes possible at the light detector 22 through the polarizing filter 24, wherein the small change is based on the coloring of the coloring reagent in the immobilized coloring reagent layer 13.

Therefore, according to the optical waveguide type glucose sensor 1i of the ninth embodiment having the structure shown in FIG. 11, it is possible to analyze with high sensitivity an extremely small amount of glucose in the solution. The reason thereof is, the optical waveguide consists of the first optical waveguide layer 2 and the second optical waveguide layer 4, and it is possible to detect the fine change of the light transmitting in the second optical waveguide layer 4 at the boundary face between the first optical waveguide layer 2 and the second optical waveguide layer 4, wherein the change of the light is caused by the coloring of the coloring reagent due to the reaction among the glucose in the solution, the enzyme and catalyst in the immobilized enzyme-catalyst layer 16 and the immobilized coloring reagent layer 13.

Then, according to the optical waveguide type glucose sensors 1b~1i from the second embodiment to the ninth embodiment, the protecting layer 5 is formed on the first optical waveguide layer 2 including the entrance grating 3a and the exit grating 3b. Thus, it is possible to prevent external stress from directly affecting the first optical waveguide layer 2, the entrance grating 3a and exit grating 3b as described in the first embodiment, and it is possible to analyze with high sensitivity an extremely small amount of glucose in the analyte 100.

In addition, according to the optical waveguide type glucose sensors 1b~1i from the second embodiment to the ninth embodiment, the stray light trapping layer 7 is formed on the surface of the protecting layer 5 excluding the inside of the opening 6. Because of this, when the transmitting light in the first optical waveguide layer 2 leaks towards the protecting layer 5 through the boundary face with the protecting layer 5, the leaked light is able to be trapped at the stray light trapping layer 7 as described in the first embodiment.

Moreover, according to the optical waveguide type glucose sensors 1b–1i from the second embodiment to the ninth embodiment, the functioning layer 8, the immobilized enzyme layer 14 or the immobilized enzyme-catalyst layer 16 is covered by the porous film 9. Due to this, an adverse effect against the functioning layer 8, the immobilized enzyme layer 14 or the immobilized enzyme-catalyst layer 16 caused by an impurity which is extracted from the analyte 100 (for example, the body fluid) or the solution can be prevented, wherein the example for the impurity is protein, blood cells or the like other than glucose. That is, due to the change based on the coloring reaction of the coloring reagent and the enzyme reaction in the functioning layer 8, the immobilized enzyme layer 14, the immobilized enzyme-catalyst layer 16 and the immobilized coloring reagent layer 13, disturbance affecting the change in the intensity of the light transmitting in the second optical waveguide layer (4 or 15) directly under the functioning layer 8 or the coloring reagent layer 13 can be reduced, and thus it is possible to analyze with even higher sensitivity an extremely small amount of glucose existing in the body fluid which is extracted from the analyte 100 or the solution.

Tenth Embodiment)

Figure 12:
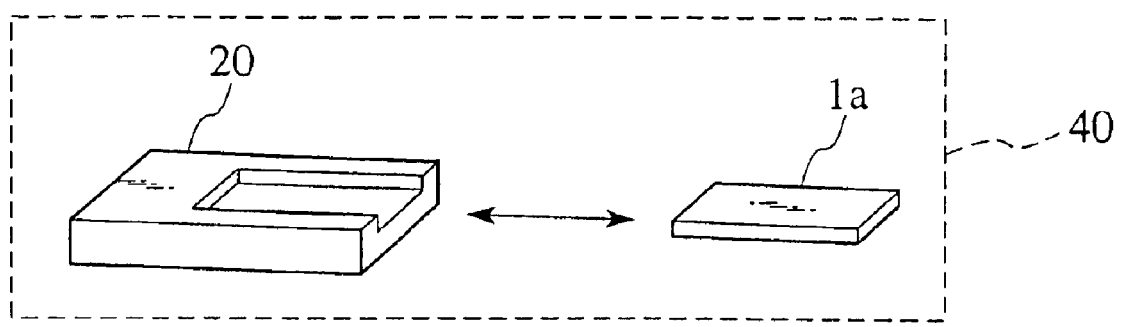
FIG. 12 is a general view showing an optical waveguide type glucose measurement device according to a tenth embodiment of the present invention.
Figure 13:
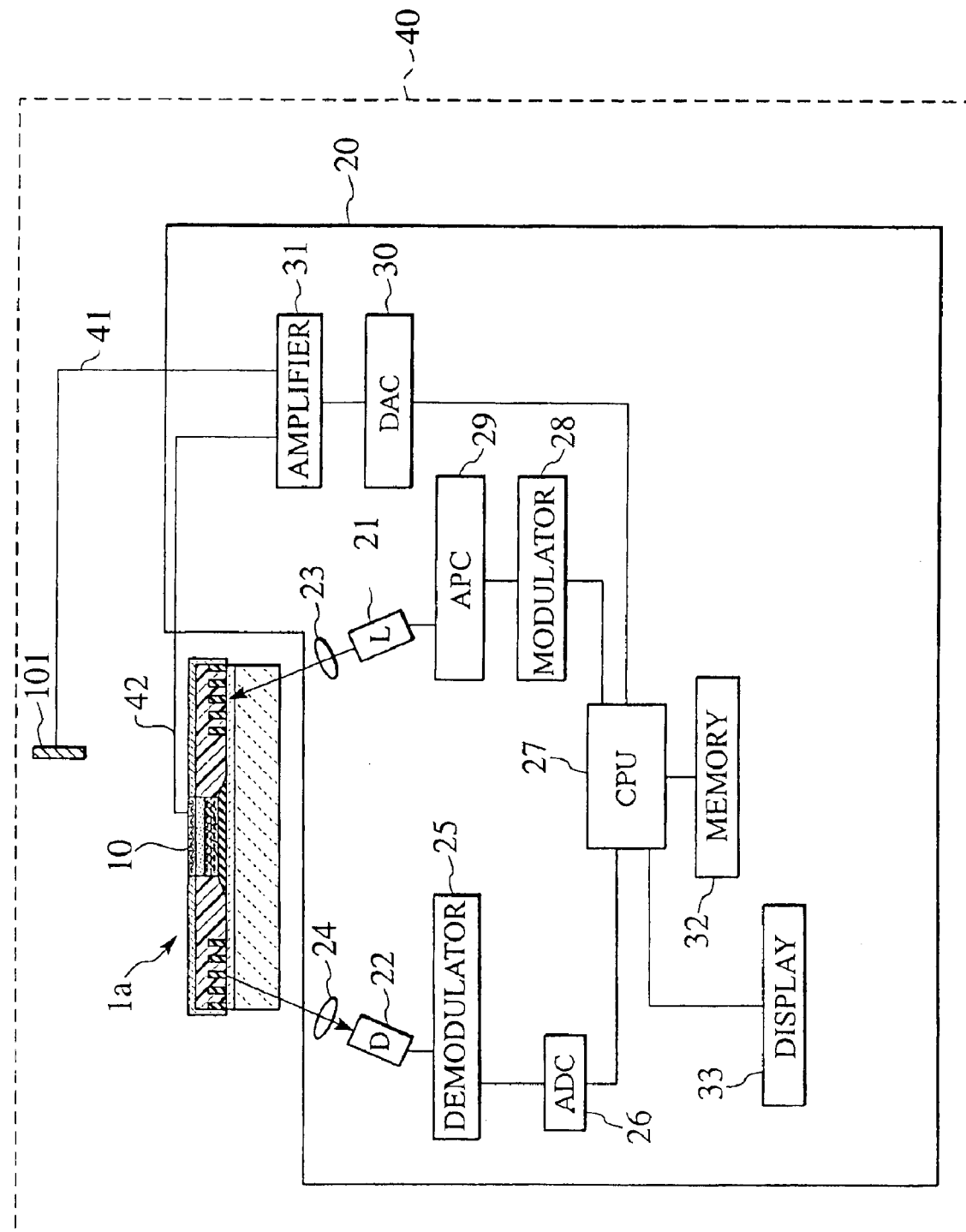
FIG. 13 is a block diagram showing a structure of the optical waveguide type glucose measurement device according to the tenth embodiment of the present invention.

The optical waveguide type glucose measuring device 40 according to the tenth embodiment, as shown in FIGS. 12 and 13, comprises a combination of the optical waveguide type glucose sensor 1a shown in FIG. 1 with a detector 20 from which the optical waveguide type glucose sensor 1a is detachable. The optical waveguide type glucose sensor 1a can be discarded after use, and the detector 20 is can be used repeatedly.

Since the structure of the optical waveguide type glucose sensor 1a has already been explained in the first embodiment, the structure of the detector 20 will be explained here.

The detector 20 comprises a central processing unit (CPU) 27. The CPU 27 is connected to a light emitter 21 such as a semiconductor laser through a modulator 28 and an automatic power controller (APC) 29, and controls the quantity of the emitted light from the light emitter 21 by a control signal thereof. The emitted light from the light emitter 21 is made incident to the substrate 1 of the optical waveguide type glucose sensor 1a through a polarizing filter 23. Moreover, the detector 20 comprises a light detector 22 such as a photodiode which receives the emitted light from the substrate 1 of the optical waveguide type glucose sensor 1a through another polarizing filter 24. The light detector 22 is connected to a demodulator 25. The demodulator 25 is connected to the CPU 27 through an A/D converter (ADC) 26.

On the other hand, the CPU 27 is connected to an amplifier 31 via a D/A converter (DAC) 30. From the amplifier 31, an anode 41 and a cathode 42 extend outside. The anode 41 connects with an electrode plate 101 at the end thereof, and the cathode 42 is for connecting to the meshed electro-conductive thin film 10.

In addition, a memory 32 in which measured data is stored and a display 33 which displays the data are connected to the CPU 27.

A procedure for the measurement of glucose using the optical waveguide type glucose measuring device 40 will be explained.

(1) The optical waveguide type glucose sensor 1a is loaded in the detector 20, an analyte is put into contact with the meshed electro-conductive thin film 10 and the electrode plate 101.

(2) The CPU 27 transmits control signals to the amplifier 31 through the DAC 30 to control the electric voltage applied to the analyte 100. Following the above signals, the voltage is applied between the meshed electro-conductive thin film 10 and the electrode plate 101 from the amplifier 31. Thus, glucose is extracted from the analyte 100 by reverse iontophoresis.

(3) The CPU 27 transmits signals to the modulator 28 which controls the quantity of the light emitted to the optical waveguide type glucose sensor 1a. The APC circuit 29 emits the quantity of light specified by the modulator 28 from the light source 21 to the optical waveguide type glucose sensor 1a.

(4) In the optical waveguide type glucose sensor 1a, the light emitted from the light source 21 is absorbed proportionally to the extracted amount of glucose through the reactions mentioned in the first embodiment. Then the remaining light is emitted from the optical waveguide type glucose sensor 1a.

(5) The emitted light from the optical waveguide type glucose sensor 1a is received by the light detector 22, and the value of the received light quantity, which is determined by the demodulator 25, is transmitted to the CPU 27 via the ADC 26.

(6) The CPU 27 calculates the difference between the light quantities, that is, the emitted quantity at the light source 21 and the received quantity at the light detector 22, stores the data which is transformed, as to glucose amount and the like when necessary in the memory 32, and displays the data on the display 33.

(7) The used optical waveguide type glucose sensor 1a is removed.

Instead of the optical waveguide type glucose sensor 1a, the optical waveguide type glucose sensors 1b and 1g maybe applied, shown in FIGS. 4 and 9 respectively. Moreover, the optical waveguide type glucose sensors 1c, 1d and 1h may be used, which do not have the meshed electro-conductive films but have the second optical waveguide layers 15, being electro-conductive, as shown in FIGS. 5, 6 and 10 respectively. However, in these cases, the cathode 42 has to be set in contact with the second optical waveguide layer 15.

In addition, in a case where the optical waveguide type glucose sensors 1e, 1f and 1i as shown in FIGS. 7, 8 and 11 are used instead of the optical waveguide type glucose sensor 1a which extracts glucose by reverse iontophoresis, the DAC 30, the amplifier 31, the anode 41 and the cathode 42 which are used for applying an electric voltage to an analyte 100, do not need to be set because they measure a glucose amount by simply dripping glucose containing solution.

Modified Example of the Tenth Embodiment

Figure 14:
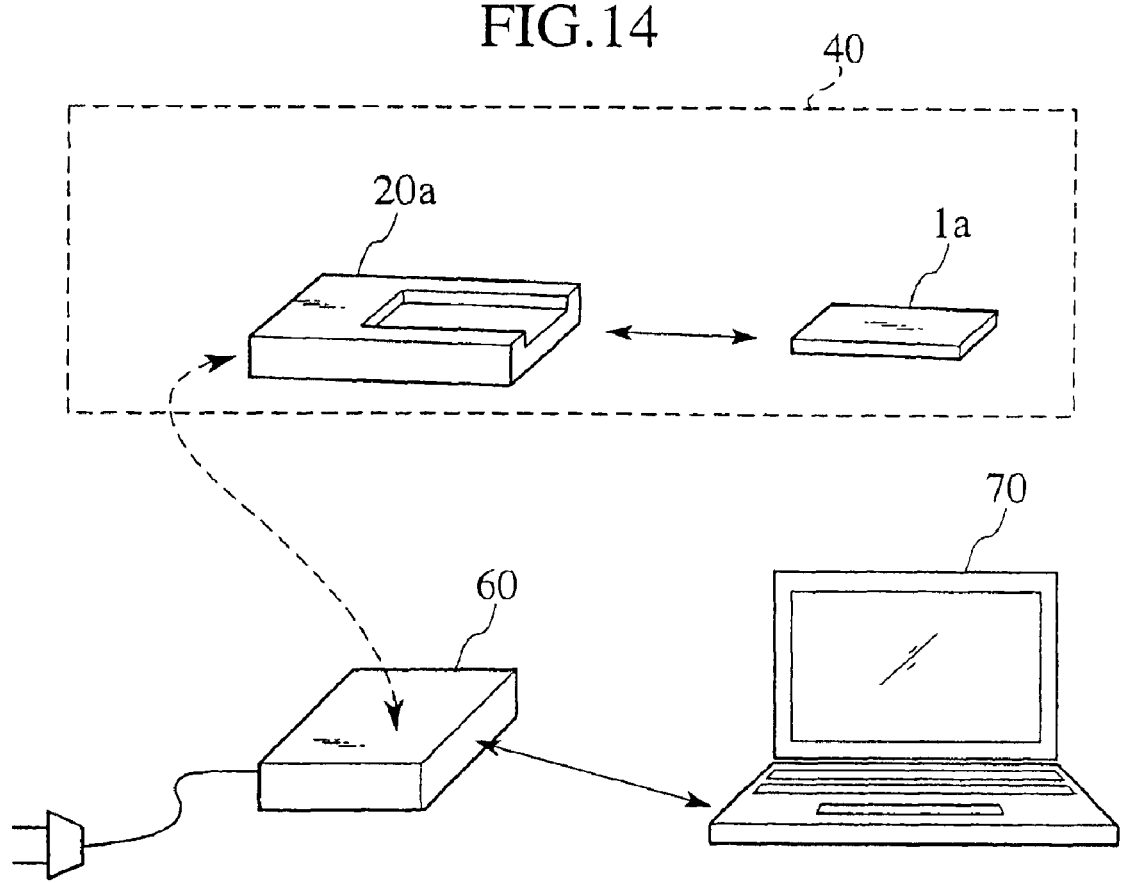
FIG. 14 is a general view showing an optical waveguide type glucose measurement device according to a modified example of the tenth embodiment of the present invention.

An optical waveguide type glucose measuring system according to the modified examples of the tenth embodiment as shown in FIG. 14, comprises the optical waveguide type glucose measuring device 40 which is a combination of the optical waveguide type glucose sensor 1a shown in FIG. 1 and the detector 20a, wherein the optical waveguide type glucose sensor 1a is detachable from the detector 20a, and a charging device 60 which connects with the detector 20a electromagnetically. In addition, the computer 70 may be connected to the charging device 60.

In terms of the structure of the detector 20a, a part which is different from the detector 20 shown in FIG. 13 will be explained referring to FIG. 15.

An electric power circuit is added to the detector 20a, wherein the electric power circuit sequentially comprises an electric power-receiving induction coil 39 which is to be connected with the charging device 60 electromagnetically, a bridge circuit 38, a nickel-hydrogen cell 37 as a secondary cell to reserve electric power which is supplied from the charging device 60 and a DC-DC converter 36 which converts an electric voltage. Then, electric power is supplied from the electric power circuit to other circuits.

In addition, a serial port 34 connected with the CPU 27, and a data transmission induction coil 35 connected with the serial port 34, are provided within the detector 20a.

Figure 16:
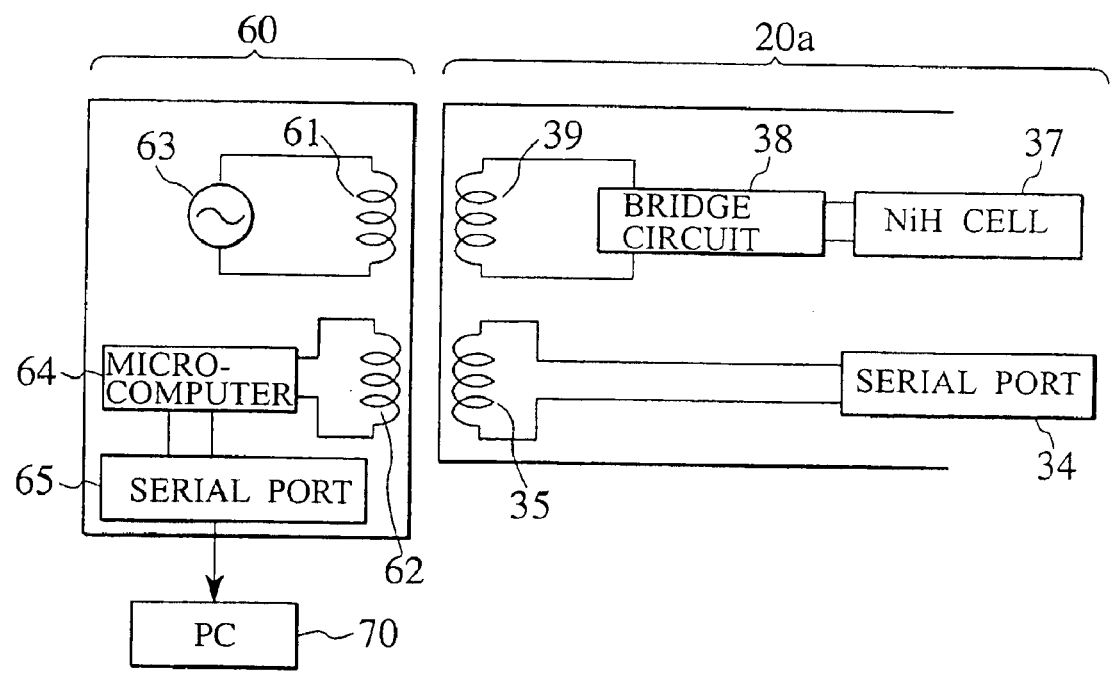
FIG. 16 is a block diagram showing a connection structure between a detector unit and a charging device according to the modified example of the tenth embodiment of the present invention.

Next, the structure of the charging device 60 will be explained referring to FIG. 16.

The charging device 60 comprises an electric power transmission induction coil 61 which is connected with an electric power-receiving induction coil 39 of the detector 20a electromagnetically, and an electric source 63 which is connected with the power transmission induction coil 61.

Moreover, the charging device 60 comprises the data-receiving induction coil 62 which is connected with a data transmission induction coil 35 of the detector 20a electromagnetically, a microcomputer 64 which transforms the data received from the detector 20a and which is connected with the data-receiving induction coil 62, and a serial port 65 which is connected with the microcomputer 64 and which is to be connected with an outside computer 70.

An operation of the optical waveguide type glucose measuring system will be explained.

(1) The detector 20a is placed within a span in which the detector 20a can be connected with the charging device 60 electromagnetically, and thus the nickel-hydrogen cell 37 in the detector 20a is charged.
(2) Measurement is conducted following the measuring procedure for glucose by use of the optical waveguide type glucose measuring device 40 mentioned in the tenth embodiment.
(3) The data measured by the optical waveguide type glucose measuring device 40 is transmitted from the data transmission induction coil 35 in the detector 20a to the data-receiving induction coil 62 which is connected with the data transmission induction coil 35 electromagnetically and which is located in the charging device 60.
(4) The data received by the charging device 60 is transferred to the outside computer 70 by the microcomputer 64 in the charging device 60.
(5) The computer 70 stores the received data in a memory, and displays data on a screen or analyzes data in response to requests.

As mentioned above, wireless charging is conducted in the optical waveguide type glucose measuring system without the optical waveguide type glucose measuring device 40 directly connected with the electric source. Moreover, the measured data may be wirelessly transferred to the computer 70 without the optical waveguide type glucose measuring device 40 connected to the computer 70 by use of a cable. Accordingly, the optical waveguide type glucose measuring device 40 is portable.

Figure 15:
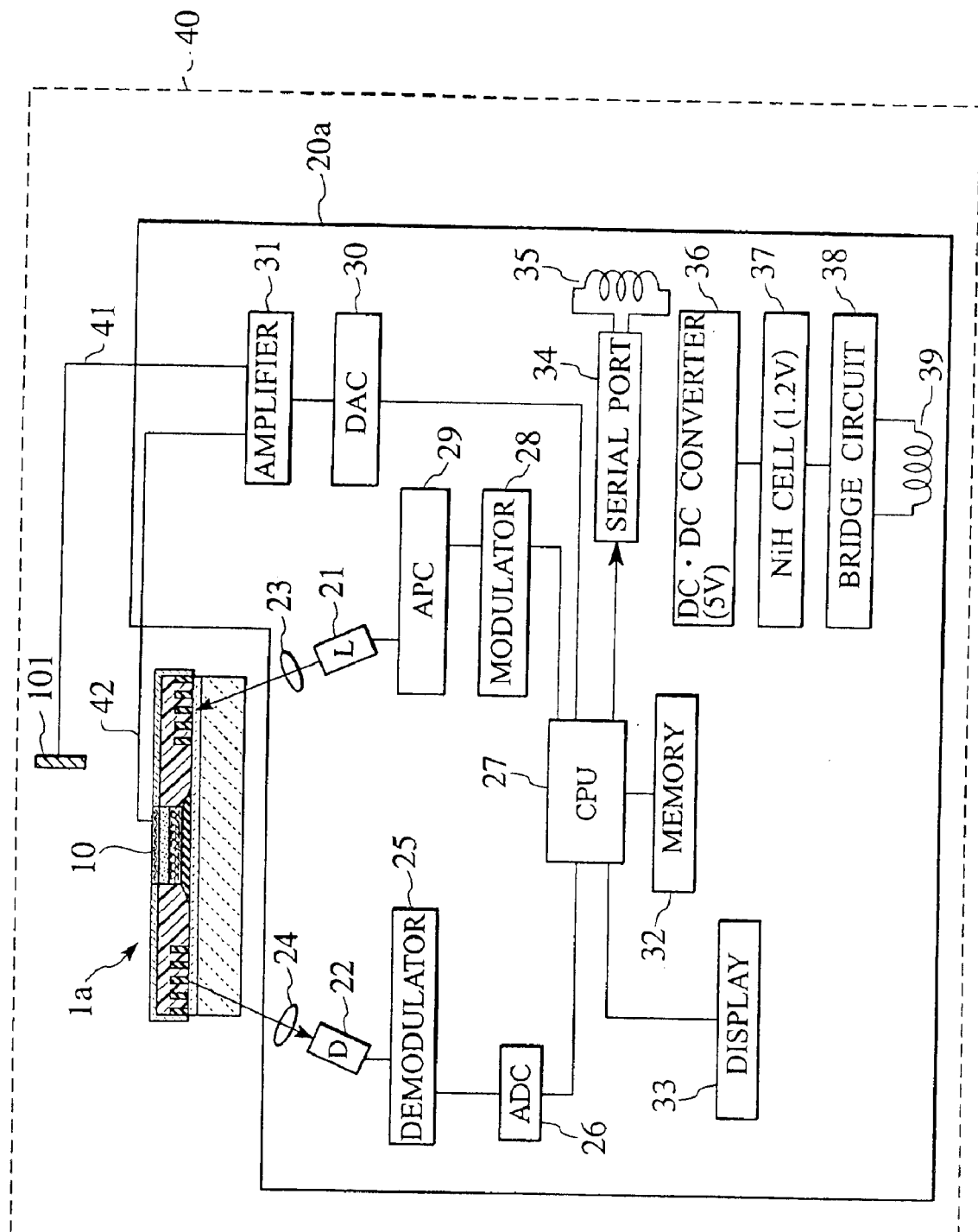
FIG. 15 is a block diagram showing a structure of the optical waveguide type glucose measuring device according to the modified example of the tenth embodiment of the present invention.

Note, a memory 32 and a display 33 are illustrated in the detector 20a in FIG. 15 but when the computer 70 is utilized, the two mentioned above are not needed specifically.

Various modifications will become possible for those skilled in the art after receiving the teachings of the present disclosure without departing from the scope thereof.

What is claimed is:

1. An optical waveguide sensor for glucose measurement comprising:
   a substrate;
   a first optical waveguide layer formed on a surface of the substrate;
   an entrance grating and an exit grating which are formed contacting with the first optical waveguide layer and being spaced from each other;
   a second optical waveguide layer located between the entrance grating and the exit grating while being in contact with the first optical waveguide layer, the second optical waveguide layer having a higher refractive index than that of the first optical waveguide layer; and
   a functioning layer containing an enzyme and a coloring reagent which is formed on the second optical waveguide layer.

2. The optical waveguide sensor of claim 1, further comprising a meshed electro-conductive thin film to which an electric field is applied and which is positioned above the functioning layer.

3. The optical waveguide sensor of claim 1, wherein the second optical waveguide layer is made of an electro-conductive material to which an electric field is applicable.

4. An optical waveguide sensor for glucose measurement, comprising:
   a substrate;
   a first optical waveguide layer formed on a surface of the substrate;
   an entrance grating and an exit grating which are formed contacting with the first optical waveguide layer and being spaced from each other;
   a second optical waveguide layer located between the entrance grating and the exit grating while being in contact with the first optical waveguide layer, the second optical waveguide layer having a higher refractive index than that of the first optical waveguide layer;
   an immobilized coloring reagent layer containing coloring reagent formed on the second optical waveguide layer; and
   an immobilized enzyme layer containing an enzyme formed on the immobilized coloring reagent layer.

5. The optical waveguide sensor of claim 4, further comprising a meshed electro-conductive thin film to which an electric field is applied and positioned above the immobilized enzyme layer.

6. The optical waveguide sensor of claim 4, wherein the second optical waveguide layer is made of an electro-conductive material to which an electric field is applicable.

7. An optical waveguide sensor for glucose measurement, comprising:
   a substrate
   a first optical waveguide layer formed on a surface of the substrate;
   an entrance grating and an exit grating which are formed contacting with the first optical waveguide layer and being spaced from each other;
   a second optical waveguide layer located between the entrance grating and the exit grating while being in contact with the first optical waveguide layer, the second optical waveguide layer having a higher refractive index than that of the first optical waveguide layer;

an immobilized coloring reagent layer containing a coloring reagent formed on the second optical waveguide layer; and an immobilized enzyme-catalyst layer containing an enzyme and a catalyst formed on the immobilized coloring reagent layer.

8. The optical waveguide sensor of claim 7, further comprising a meshed electro-conductive thin film to which an electric field is applied and positioned above the immobilized enzyme-catalyst layer.

9. The optical waveguide sensor of claim 7, wherein the second optical waveguide layer is made of an electro-conductive material to which an electric field is applicable.

10. An optical waveguide device for glucose measurement, comprising:
an optical waveguide sensor, comprising:
a substrate,
a first optical waveguide layer formed on a surface of the substrate,
an entrance grating and an exit grating contacting with the first optical waveguide layer and being spaced from each other,
a second optical waveguide layer located between the entrance grating and the exit grating while being in contact with the first optical waveguide layer, the second optical waveguide layer having a higher refractive index than that of the first optical waveguide layer, and
a functioning layer containing an enzyme and a coloring reagent formed on the second optical waveguide layer; and
a detection unit, comprising:
a light source configured to emit a light to the first optical waveguide layer,
a light detector configured to receive the light coming from the first optical waveguide layer,
a central process control unit configured to control a light quantity of the light source and process signals from the light detector,
a memory configured to store data from the central process control unit, and
a display configured to display the data.

11. The optical waveguide device of claim 10, wherein the optical waveguide sensor, further comprises:
a meshed electro-conductive thin film formed above the functioning layer; and
the detection unit, further comprises:
a cathode configured to contact with the meshed electro-conductive thin film, and
an anode having an end to which an electrode plate is connected, and
wherein the central process control unit controls an electric voltage applied between the cathode and the anode.

12. The optical waveguide device of claim 10, wherein the detection unit, further comprises:
a cathode configured to contact with the second optical waveguide layer, and
an anode having an end to which an electrode plate is connected, and
wherein the central process control unit controls an electric voltage applied between the cathode and the anode.

13. An optical waveguide device for glucose measurement, comprising:
an optical waveguide sensor, comprising:
a substrate,
a first optical waveguide layer formed on a surface of the substrate,
an entrance grating and an exit grating contacting with the first optical waveguide layer and being spaced from each other;
a second optical waveguide layer located between the entrance grating and the exit grating while being in contact with the first optical waveguide layer, the second optical waveguide layer having a higher refractive index than that of the first optical waveguide layer,
an immobilized coloring reagent layer containing a coloring reagent formed on the second optical waveguide layer, and
an immobilized enzyme layer containing an enzyme formed on the immobilized coloring reagent layer; and
a detection unit, comprising:
a light source configured to emit a light to the first optical waveguide layer,
a light detector configured to receive the light coming from the first optical waveguide layer,
a central process control unit configured to control a light quantity of the light source and process signals from the light detector,
a memory configured to store data from the central process control unit, and
a display configured to display the data.

14. The optical waveguide device of claim 13, wherein the optical waveguide sensor, further comprises:
a meshed electro-conductive thin film formed above the immobilized enzyme layer; and
the detection unit, further comprises:
a cathode configured to contact with the meshed electro-conductive thin film, and
an anode having an end to which an electrode plate is connected, and
wherein the central process control unit controls an electric voltage applied between the cathode and the anode.

15. The optical waveguide device of claim 13, wherein the detection unit, further comprises:
a cathode configured to contact with the second optical waveguide layer, and
an anode having an end to which an electrode plate is connected, and
wherein the central process control unit controls an electric voltage applied between the cathode and the anode.

16. An optical waveguide device for glucose measurement, comprising:
an optical waveguide sensor, comprising:
a substrate,
a first optical waveguide layer formed on a surface of the substrate,
an entrance grating and an exit grating contacting with the first optical waveguide layer and being spaced from each other,
a second optical waveguide layer located between the entrance grating and the exit grating while being in contact with the first optical waveguide layer, the second optical waveguide layer having a higher refractive index than that of the first optical waveguide layer,
an immobilized coloring reagent layer containing a coloring reagent formed on the second optical waveguide layer, and an immobilized enzyme-catalyst layer containing an enzyme and a catalyst formed on the immobilized coloring reagent layer; and a detection unit, comprising:
  a light source configured to emit a light to the first optical waveguide layer,
  a light detector configured to receive the light coming from the first optical waveguide layer,
  a central process control unit configured to control a light quantity of the light source and processes signals from the light detector,
  a memory configured to store data from the central process control unit, and
  a display configured to display the data.

17. The optical waveguide device of claim 16; wherein the optical waveguide sensor, further comprises:
  a meshed electro-conductive thin film formed above the immobilized enzyme-catalyst layer; and
  the detection unit, further comprises:
    a cathode configured to contact with the meshed electro-conductive thin film, and
    an anode having an end to which an electrode plate is connected, and
  wherein the central process control unit controls an electric voltage applied between the cathode and the anode.

18. The optical waveguide device of claim 16, wherein the detection unit, further comprises:
  a cathode configured to contact with the second optical waveguide layer, and
  an anode having an end to which an electrode plate is connected, and
  wherein the central process control unit controls an electric voltage applied between the cathode and the anode.

19. An optical waveguide system for glucose measurement, comprising:
  an optical waveguide device, comprising:
    an optical waveguide sensor, comprising:
      a substrate,
      a first optical waveguide layer formed on a surface of the substrate,
      an entrance grating and an exit grating contacting with the first optical waveguide layer and being spaced from each other,
      a second optical waveguide layer located between the entrance grating and the exit grating while being in contact with the first optical waveguide layer, the second optical waveguide layer having a higher refractive index than that of the first optical waveguide layer,
      a functioning layer containing an enzyme and a coloring reagent formed on the second optical waveguide layer, and
      a meshed electro-conductive thin film positioned above the functioning layer, and
    a detection unit, comprising:
      a light source configured to emit a light to the first optical waveguide layer,
      a light detector configured to receive the light coming from the first optical waveguide layer,
      a cathode configured to contact with the meshed electro-conductive thin film,
      an anode having an end to which an electrode plate is connected,
      a central process control unit configured to control a light quantity of the light source, to process signals sent from the light detector and to control an electric voltage applied between the cathode and the anode,
      an electric power supply circuit having an electric power-receiving induction coil,
      a serial port connected to the central process control unit, and
      a data transmission induction coil connected to the serial port; and
    a charging device, comprising:
      an electric power transmission induction coil and a data-receiving induction coil connected with the electric power-receiving induction coil and the data transmission induction coil located in the detection unit electromagnetically, and
      a microcomputer configured to transfer data received by the data-receiving induction coil to an outside computer.

20. An optical waveguide system for glucose measurement, comprising:
  an optical waveguide device, comprising:
    an optical waveguide sensor, comprising:
      a substrate,
      a first optical waveguide layer formed on a surface of the substrate,
      an entrance grating and an exit grating contacting with the first optical waveguide layer and being spaced from each other,
      a second optical waveguide layer located between the entrance grating and the exit grating while being in contact with the first optical waveguide layer, the second optical waveguide layer having a higher refractive index than that of the first optical waveguide layer, and
      a functioning layer containing an enzyme and a coloring reagent formed on the second optical waveguide layer, and
    a detection unit, comprising:
      a light source configured to emit a light to the first optical waveguide layer,
      a light detector configured to receive the light coming from the first optical waveguide layer,
      a cathode configured to contact with the second optical waveguide layer,
      an anode having an end to which an electrode plate is connected,
      a central process control unit configured to control a light quantity of the light source, to process signals from the light detector and to control an electric voltage applied between the cathode and the anode,
      an electric power supply circuit having an electric power-receiving induction coil,
      a serial port connected to the central process control unit, and
      a data transmission induction coil connected to the serial port; and
    a charging device, comprising:
      an electric power transmission induction coil and a data-receiving induction coil connected with the electric power-receiving induction coil and the data transmission induction coil located in the detection unit electromagnetically, and
      a microcomputer configured to transfer data received by the data-receiving induction coil to an outside computer.

* * * * *